United States Patent
Turng et al.

(10) Patent No.: US 11,786,639 B2
(45) Date of Patent: Oct. 17, 2023

(54) PROMOTING ENDOTHELIAL CELL AFFINITY AND ANTITHROMBOGENICITY OF POLYTETRAFLUOROETHYLENE (PTFE) BY MUSSEL-INSPIRED MODIFICATION AND RGD/HEPARIN GRAFTING

(71) Applicant: Wisconsin Alumni Research Foundation, Madison, WI (US)

(72) Inventors: Lih-Sheng Turng, Madison, WI (US); Hao-yang Mi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/935,300

(22) Filed: Sep. 26, 2022

(65) Prior Publication Data
US 2023/0026861 A1    Jan. 26, 2023

Related U.S. Application Data

(62) Division of application No. 16/426,192, filed on May 30, 2019, now Pat. No. 11,484,626.

(60) Provisional application No. 62/677,939, filed on May 30, 2018.

(51) Int. Cl.
| | | |
|---|---|---|
| A61L 27/26 | (2006.01) | |
| A61L 27/50 | (2006.01) | |
| A61L 27/54 | (2006.01) | |
| C08L 67/02 | (2006.01) | |
| A61L 27/18 | (2006.01) | |
| A61L 33/00 | (2006.01) | |

(52) U.S. Cl.
CPC .............. *A61L 27/507* (2013.01); *A61L 27/18* (2013.01); *A61L 27/54* (2013.01); *A61L 33/0023* (2013.01); *C08L 67/02* (2013.01); *A61F 2310/00389* (2013.01); *A61L 2300/42* (2013.01)

(58) Field of Classification Search
CPC ........ A61L 27/507; A61L 27/18; A61L 27/54; A61L 33/0023; A61L 2300/42; C08L 67/02; A61F 2310/00389
See application file for complete search history.

(56) References Cited

U.S. PATENT DOCUMENTS

| | | |
|---|---|---|
| 2005/0027364 A1 | 2/2005 | Kim et al. |
| 2008/0149566 A1 | 6/2008 | Messersmith et al. |
| 2016/0302911 A1 | 10/2016 | Soletti |
| 2017/0173226 A1 | 6/2017 | Hai et al. |

FOREIGN PATENT DOCUMENTS

| | | |
|---|---|---|
| WO | 2016187698 A1 | 1/2016 |
| WO | 2018053265 A1 | 3/2018 |

OTHER PUBLICATIONS

Mil et al., Promoting Endothelial Cell Affinity and Antithrombogenicity of Polytetrafluoreothylene (PTFE) by Mussel-inspired Modification and RGD/Heparin Grafting; J. Maler Chem B; 2018, vol. 6, pp. 3475-3485.
Ravi et al., Biomaterials for vascular tissue engineering; Regen Med., 2010, vol. 5, No. 1, 21 pages.
Yu et al., Development of Biomimelic Thermoplastic Polyurelhane/Fibroin Small-Diameter Vascular Grafts via a Novel Electrospinning Approach; J. Biomed Maier Res A.; 2018; vol. 106, No. 4. pp. 985-996.

*Primary Examiner* — Alma Pipic
(74) *Attorney, Agent, or Firm* — Stinson LLP

(57) ABSTRACT

Disclosed herein are methods for modifying a substrate having a hydrophobic surface. Also disclosed are modified hydrophobic substrates. The modified hydrophobic substrates and methods disclosed herein advantageously improve cell affinity and antithrombogenicity of hydrophobic surfaces.

7 Claims, 18 Drawing Sheets
Specification includes a Sequence Listing.

without plasma treatment     with plasma treatment

PROMOTING ENDOTHELIAL CELL AFFINITY AND ANTITHROMBOGENICITY OF POLYTETRAFLUOROETHYLENE (PTFE) BY MUSSEL-INSPIRED MODIFICATION AND RGD/HEPARIN GRAFTING

CROSS REFERENCE TO RELATED APPLICATIONS

This application is a divisional application of U.S. application Ser. No. 16/426,192 filed May 30, 2019, which claims priority to U.S. Provisional Application No. 62/677,939 filed on May 30, 2018, the disclosures of which are hereby incorporated by reference in their entireties.

STATEMENT OF GOVERNMENT SUPPORT

This invention was made with government support under HL134655 awarded by the National Institutes of Health. The government has certain rights in the invention.

INCORPORATION OF SEQUENCE LISTING

A computer readable form of the Sequence Listing containing the file named "3004049.0120 Sequence Listing xml", which is, 519 bytes in size (as measured in MICROSOFT WINDOWS® EXPLORER) and generated on Sep. 21, 2022, are provided herein and are herein incorporated by reference. This Sequence Listing consists of SEQ ID NOs: 1-4.

BACKGROUND OF THE DISCLOSURE

The present disclosure relates generally to tissue engineering. In particular, the present disclosure relates to methods for modifying hydrophobic materials. The present disclosure relates to modified hydrophobic substrates. The modified hydrophobic substrates and methods disclosed herein advantageously improve cell affinity and antithrombogenicity of hydrophobic surfaces.

Prosthetic vascular grafts, namely polyethylene terephthalate (PET, Dacron) and expanded polytetrafluoroethylene (ePTFE), have been successfully utilized as large-diameter vessel replacements owing to their high mechanical strength, flexibility, biocompatibility, and commercial availability. The massive blood flow in large-diameter blood vessels aids in the prevention of blood clots. However, the long-term patency of prosthetic vascular grafts is discouraging in small diameter vascular grafts (SDVGs) (<6 mm) due to the high risk of luminal thrombosis that is caused by a lack of endothelial cells and anastomotic intimal hyperplasia. The primary physiological function of endothelial cells is to facilitate blood flow by providing a suitable hemocompatible and antithrombogenic surface. Thus, mimicking the native physiological structure and properties of blood vessels by vascular tissue engineering strategies have been proposed and have become an important topic in biomedical engineering.

Various biodegradable synthetic materials, such as poly (lactic acid) (PLA), poly (lactic-co-glycolic acid) (PLGA), poly (ε-caprolactone) (PCL), and polyurethane (PU), have been employed to fabricate SDVGs. Although these materials have been found to be biocompatible with endothelial cells, they suffer from a slow endothelialization rate and a high risk of thrombosis. Improving the endothelial cell affinity and antithrombogenicity of synthetic SDVGs present challenges for vascular tissue engineering. The major reason for inferior endothelial cell affinity is the lack of bioactive binding sites on these hydrophobic materials. Therefore, surface modification is highly desired for promoting the bioactivity of synthetic materials since surface modification has the unique advantage of altering the surface chemistry without interfering with the material's bulk properties. Hydrophobic surfaces are typically difficult to modify, especially in an aqueous environment, due to the lack of hydrophilic functional groups.

Plasma treatment is a practical physical modification approach for altering a material's surface energy. Earlier studies demonstrated the positive effect of plasma treatment on improving PTFE biocompatibility. For example, ammonia-plasma-treated PET and PTFE showed the enhanced adhesion and growth of endothelial cells and the slightly upregulated expression of adhesion molecules. Amide- and amine-plasma-treated PTFE showed an enhanced endothelial cell lining and stimulated the formation of an endothelial cell monolayer. However, the functional groups introduced via plasma treatment are limited and the introduced hydrophilic groups are not stable long-term.

Improving the antithrombogenicity is highly desirable. Introducing an endothelial cell layer provides a solution for the prevention of thrombosis in vascular tissue engineering, but the risk is still present if the surface is not fully covered by an endothelial cell layer. Thus, rapid endothelialization is desirable. The incorporation of heparin is another effective way to improve antithrombogenicity due to its anticoagulation properties. Various heparin-modified materials, such as chitosan/graphene oxide hydrogels, collagen-coated PTFEs, porous PLA membranes, and decellularized matrices, show reduced platelet adhesion. Heparin molecules may gradually release into the blood flow and cause low sustainability in long-term implantation applications. For this reason, fast endothelialization may remedy the gradually decreasing heparin level.

Arginine-glycine-aspartic acid (RGD), a tri-amino acid sequence, is the most common peptide motif responsible for cell adhesion to the extracellular matrix (ECM) and has been used extensively to enhance cell attachment on biomaterials. Since RGD is readily dissolved in water, it has to be chemically grafted onto a substrate. But, grafting of RGD onto hydrophobic surfaces is fairly difficult. A practical solution is to combine a hydrophobic polymer with a hydrophilic material like alginate or collagen prior to RGD grafting. However, this approach deteriorates the mechanical property advantages of synthetic polymers and increases fabrication cost.

In view of the foregoing, alternative methods for enhancing endothelial cell affinity and antithrombogenicity of synthetic biomaterials that contain hydrophobic surfaces used in vascular grafts is needed.

BRIEF DESCRIPTION

Disclosed herein are methods for modifying hydrophobic surfaces of synthetic materials. Also disclosed are modified hydrophobic substrates. The method allows for the attachment of biomolecules on hydrophobic surfaces, which can promote cell affinity and reduce thrombogenicity of synthetic biomaterials used in vascular grafts.

In one aspect, the present disclosure is directed to a method for modifying a hydrophobic surface, the method comprising: treating the hydrophobic surface with oxygen plasma to form an oxygen plasma-treated surface; coating the oxygen plasma-treated surface with a solution comprising dopamine to form a dopamine-coated surface; coating the dopamine-coated surface with a solution comprising polymer comprising a terminal amine to form a polymer coating on the dopamine-coated surface; and immobilizing a bioactive molecule on the polymer coating by contacting the bioactive molecule with the polymer coating.

In one aspect, the present disclosure is directed to a method for modifying a substrate comprising a hydrophobic surface, the method comprising: treating the hydrophobic surface with oxygen plasma to form an oxygen plasma-treated surface; coating the oxygen plasma-treated surface with a solution comprising dopamine to form a dopamine-coated surface; coating the dopamine-coated surface with a solution comprising a polymer comprising a terminal amine to form a polymer coating on the dopamine-coated surface; and immobilizing a bioactive molecule on the polymer coating by contacting the bioactive molecule with the polymer coating.

In one aspect, the present disclosure is directed to a modified hydrophobic substrate comprising a substrate comprising a hydrophobic surface, a first layer comprising dopamine disposed on the substrate, and a second layer comprising a free amine disposed on the first layer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein.

DETAILED DESCRIPTION

Figure 1:
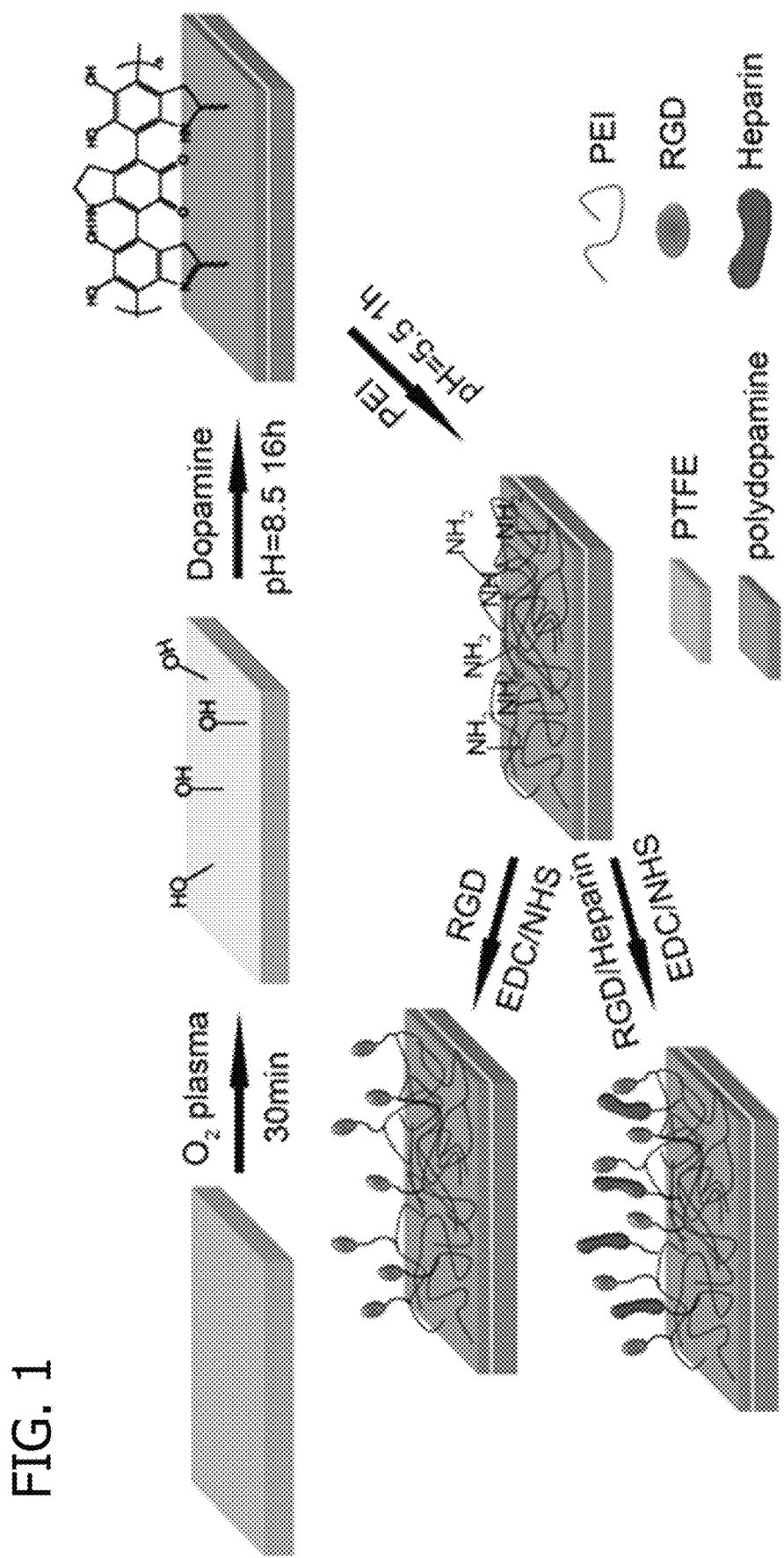
FIG. 1 is a schematic depicting the surface modification procedure using PTFE. PTFE was first treated with $O_2$ plasma to obtain P-PTFE, dopamine (DA) was polymerized on P-PTFE to obtain DA-PTFE, then PEI was immobilized on DA-PTFE, followed by the grafting of RGD or RGD/heparin to obtain RGD-PTFE or R/H-PTFE, respectively.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In one aspect, the present disclosure is directed to a method for modifying a hydrophobic surface, the method comprising: treating the hydrophobic surface with oxygen plasma to form an oxygen plasma-treated surface; coating the oxygen plasma-treated surface with a solution comprising dopamine to form a dopamine-coated surface; coating the dopamine-coated surface with a solution comprising polymer comprising a terminal amine to form a polymer coating on the dopamine-coated surface; and immobilizing a bioactive molecule on the polymer coating by contacting the bioactive molecule with the polymer coating.

Any suitable method for treating the hydrophobic surface with oxygen plasma can be used. Commercially available plasma etchers (e.g., PlasmaEtch PE-200) can be used to oxygen plasma treat the hydrophobic surfaces.

The hydrophobic surfaces include polytetrafluoroethylene (PTFE), poly (lactic acid) (PLA), poly (lactic-co-glycolic acid) (PLGA), poly (ε-caprolactone) (PCL), polyurethane (PU), polypropylene carbonate (PPC), polyhydroxybutyrate (PHB), and the like, and combinations thereof.

The dopamine coating can be prepared by contacting the oxygen plasma-treated surface with a solution comprising dopamine to form the dopamine-coated surface. For example, the oxygen plasma-treated surface can be immersed into a dopamine solution for a sufficient period of time to form the dopamine coating. The concentration of dopamine in the dopamine solution can range from about 0.5 mg/mL to about 5 mg/mL.

The method then includes coating the dopamine-coated surface with a solution comprising a polymer having a terminal amine to form a polymer coating on the dopamine-coated surface. Suitable polymers having a terminal amine include, for example, polyethylenimine (PEI), polyethyleneglycol (PEG)-amine, polyalkylene oxide (PAO)-amine, polyallylamine, polyvinylamine, poly(vinylamine-co-vinylformamide), chitosan-amine, and poly(amidoamine). The polyethyleneimine suitably can be linear, dendritic, comb, or branched. To coat the dopamine-coated surface with the polymer, the dopamine-coated surface can be immersed in a solution containing the polymer for a suitable period of time such that a polymer film forms. The polymer in the solution can range from about 0.1 mg/mL to about 1 mg/mL. The polymer coating introduces amino groups onto the dopamine-coated surface. The thickness of the polymer coating can range from molecular scale to tens of nanometers.

The method then includes immobilizing a bioactive molecule on the polymer coating. The bioactive molecule is immobilized by contacting the bioactive molecule with the polymer coating. A particularly suitable method is by (1-ethyl-3-(3-dimethylaminopropyl)-carbodiimide) (EDC)/ N-hydroxysuccinimide (NHS) coupling chemistry.

Any bioactive molecule can be immobilized. Suitable bioactive molecules include any biomolecule having carboxyl groups and being water soluble. A suitable bioactive molecule includes a cell adhesion molecule. Suitable cell adhesion molecules include fibronectin, arginine-glycine-aspartic acid (RGD) peptide, arginine-glycine-aspartic acid-serine (RGDS) peptide (SEQ ID NO:1), leucine-aspartic acid-valine (LDV) peptide, fibronectin CS1 region, laminin, tyrosine-isoleucine-glycine-serine-arginine (YIGSR) peptide (SEQ ID NO:2), proline-aspartic acid-serine-glycine-arginine (PDSGR) peptide (SEQ ID NO:3), lysine-arginine-glutamic acid (LRE) peptide, vitronectin, arginine-glycine-aspartic acid-valine (RGDV) peptide (SEQ ID NO:4), and combinations thereof. Other suitable bioactive molecules include anticoagulants. Suitable anticoagulants include heparin, low molecular weight heparin, a coumarin, a directly acting oral anticoagulants (DOACs), fondaparinux, idraparinux, a factor Xa inhibitor, a thrombin inhibitor, hementin, and combinations thereof. Suitable coumarins include warfarin, acenocoumarol, phenprocoumon, atromentin, and phenindione. Suitable directly acting oral anticoagulants (DOACs) include dabigatran, rivaroxaban, apixaban, edoxaban and betrixaban. Suitable factor Xa inhibitors include rivaroxaban, apixaban, edoxaban, betrixaban, darexaban, letaxaban, and eribaxaban. Suitable thrombin inhibitors include hirudin, lepirudin, bivalirudin, argatroban, dabigatran, ximelagatran and combinations thereof.

In one embodiment at least two bioactive molecules can be immobilized on the polymer coating. Suitably, one of the at least two bioactive molecules is a cell adhesion molecule and the other of the at least two bioactive molecules is an anticoagulant. Suitably, one of the at least two bioactive molecules is a RGD peptide and the other of the at least two bioactive molecules is heparin.

The method can further include seeding a cell on the modified substrate. Suitable cells include endothelial cells, smooth muscle cells, mesenchymal stem cells, umbilical vein endothelial cells, fibroblast cells, and combinations thereof. The seeded cells can then be cultured for a sufficient period of time for cells to migrate, proliferate and differentiate.

In one embodiment, the hydrophobic surface is a hydrophobic surface of a vascular graft. Suitable vascular grafts include large diameter vascular grafts, small diameter vascular grafts, and combinations thereof. As used herein, "small-diameter vascular graft" refers to an artificial vascular graft that is made of biocompatible materials and having a lumen diameter less than 6 mm. As used herein, "large-diameter vascular graft" refers to an artificial vascular graft that is made of biocompatible materials and having a lumen diameter greater than 6 mm.

In another aspect, the present disclosure is directed to a method for modifying a substrate comprising a hydrophobic surface, the method comprising: treating the hydrophobic surface with oxygen plasma to form an oxygen plasma-treated surface; coating the oxygen plasma-treated surface with a solution comprising dopamine to form a dopamine-coated surface; coating the dopamine-coated surface with a solution comprising a polymer comprising a terminal amine to form a polymer coating on the dopamine-coated surface; and immobilizing a bioactive molecule on the polymer coating by contacting the bioactive molecule with the polymer coating.

Suitable substrates include glasses, metals, woods, cotton, plastics, ceramics, and combinations thereof.

Any suitable method for treating the hydrophobic surface with oxygen plasma can be used. Commercially available plasma etchers (e.g., PlasmaEtch PE-200) can be used to oxygen plasma treat the hydrophobic surfaces.

The hydrophobic surfaces include polytetrafluoroethylene (PTFE), poly (lactic acid) (PLA), poly (lactic-co-glycolic acid) (PLGA), poly (ε-caprolactone) (PCL), polyurethane (PU), polypropylene carbonate (PPC), polyhydroxybutyrate (PHB) and combinations thereof.

The dopamine coating can be prepared by contacting the oxygen plasma-treated surface with a solution comprising dopamine to form the dopamine-coated surface. For example, the oxygen plasma-treated surface can be immersed into a dopamine solution for a sufficient period of time to form the dopamine coating. The concentration of dopamine in the dopamine solution can range from about 0.5 mg/mL to about 5 mg/mL.

The method then includes coating the dopamine-coated surface with a solution comprising a polymer having a terminal amine to form a polymer coating on the dopamine-coated surface. Suitable polymers having a terminal amine include, for example, polyethylenimine (PEI), polyethyleneglycol (PEG)-amine, polyalkylene oxide (PAO)-amine, polyallylamine, polyvinylamine, poly(vinylamine-co-vinylformamide), chitosan-amine, and poly(amidoamine). The polyethyleneimine suitably can be linear, dendritic, comb, or branched. To coat the dopamine-coated surface with the polymer, the dopamine-coated surface can be immersed in a solution containing the polymer for a suitable period of time such that a the polymer film forms. The polymer in the solution can range from about 0.1 mg/mL to about 1 mg/mL. The polymer coating introduces amino groups onto the dopamine-coated surface. The thickness of the polymer coating can range from molecular scale to tens of nanometers.

The method then includes immobilizing a bioactive molecule on the polymer coating. The bioactive molecule is immobilized by contacting the bioactive molecule with the polymer coating. A particularly suitable method is by (1-ethyl-3-(3-dimethylaminopropyl)-carbodiimide) (EDC)/ N-hydroxysuccinimide (NHS) coupling chemistry.

Any bioactive molecule can be immobilized. Suitable bioactive molecules include any biomolecule having carboxyl groups and being water soluble. A suitable bioactive molecule includes a cell adhesion molecule. Suitable cell adhesion molecules include fibronectin, arginine-glycine-aspartic acid (RGD) peptide, arginine-glycine-aspartic acid-serine (RGDS) peptide (SEQ ID NO:1), leucine-aspartic acid-valine (LDV) peptide, fibronectin CS1 region, laminin, tyrosine-isoleucine-glycine-serine-arginine (YIGSR) peptide (SEQ ID NO:2), proline-aspartic acid-serine-glycine-arginine (PDSGR) peptide (SEQ ID NO:3), lysine-arginine-glutamic acid (LRE) peptide, vitronectin, arginine-glycine-aspartic acid-valine (RGDV) peptide (SEQ ID NO:4), and combinations thereof. Other suitable bioactive molecules include anticoagulants. Suitable anticoagulants include heparin, low molecular weight heparin, a coumarin, a directly acting oral anticoagulants (DOACs), fondaparinux, idraparinux, a factor Xa inhibitor, a thrombin inhibitor, hementin, and combinations thereof. Suitable coumarins include warfarin, acenocoumarol, phenprocoumon, atromentin, and phenindione. Suitable directly acting oral anticoagulants (DOACs) include dabigatran, rivaroxaban, apixaban, edoxaban and betrixaban. Suitable factor Xa inhibitors include rivaroxaban, apixaban, edoxaban, betrixaban, darexaban, letaxaban, and eribaxaban. Suitable thrombin inhibitors include hirudin, lepirudin, bivalirudin, argatroban, dabigatran, ximelagatran and combinations thereof.

In one embodiment at least two bioactive molecules can be immobilized on the PEI coating. Suitably, one of the at least two bioactive molecules is a cell adhesion molecule and the other of the at least two bioactive molecules is an anticoagulated. Suitably, one of the at least two bioactive molecules is a RGD peptide and the other of the at least two bioactive molecules is heparin.

The method can further include seeding a cell on the modified substrate. Suitable cells include endothelial cells, smooth muscle cells, mesenchymal stem cells, umbilical vein endothelial cells, fibroblast cells, and combinations thereof. The seeded cells can then be cultured for a sufficient period of time for cells to migrate, proliferate and differentiate.

In one embodiment, the hydrophobic surface is a hydrophobic surface of a vascular graft. Suitable vascular grafts include large diameter vascular grafts, small diameter vascular grafts, and combinations thereof.

In one aspect, the present disclosure is directed to a modified hydrophobic substrate comprising a substrate comprising a hydrophobic surface, a first layer comprising dopamine disposed on the substrate, and a second layer comprising a polymer comprising a terminal amine disposed on the first layer.

In one embodiment, the hydrophobic surface is an oxygen plasma treated surface.

In one embodiment, the hydrophobic surface is a surface of a substrate. Suitable substrates include glasses, metals, woods, cotton, plastics, ceramics, and combinations thereof.

The second layer includes a polymer having a terminal amine. Suitable polymers having a terminal amine include, for example, polyethylenimine (PEI), polyethyleneglycol (PEG)-amine, polyalkylene oxide (PAO)-amine, polyallylamine, polyvinylamine, poly(vinylamine-co-vinylformamide), chitosan-amine, and poly(amidoamine). The polyethyleneimine suitably can be linear, dendritic, comb, or branched.

The polymer having a terminal amine is covalently bonded to the first layer comprising dopamine.

The modified hydrophobic substrate can further include a third layer having at least one biomolecule. Suitable bioactive molecules include any biomolecule having carboxyl groups and are water soluble. A suitable bioactive molecule includes a cell adhesion molecule. Suitable cell adhesion molecules include fibronectin, arginine-glycine-aspartic acid (RGD) peptide, arginine-glycine-aspartic acid-serine (RGDS) peptide (SEQ ID NO:1), leucine-aspartic acid-valine (LDV) peptide, fibronectin CS1 region, laminin, tyrosine-isoleucine-glycine-serine-arginine (YIGSR) peptide (SEQ ID NO:2), proline-aspartic acid-serine-glycine-arginine (PDSGR) peptide (SEQ ID NO:3), lysine-arginine-glutamic acid (LRE) peptide, vitronectin, arginine-glycine-aspartic acid-valine (RGDV) peptide (SEQ ID NO:4), and combinations thereof. Other suitable bioactive molecules include anticoagulants. Suitable anticoagulants include heparin, low molecular weight heparin, a coumarin, a directly acting oral anticoagulants (DOACs), fondaparinux, idraparinux, a factor Xa inhibitor, a thrombin inhibitor, hementin, and combinations thereof. Suitable coumarins include warfarin, acenocoumarol, phenprocoumon, atromentin, and phenindione. Suitable directly acting oral anticoagulants (DOACs) include dabigatran, rivaroxaban, apixaban, edoxaban and betrixaban. Suitable factor Xa inhibitors include rivaroxaban, apixaban, edoxaban, betrixaban, darexaban, letaxaban, and eribaxaban. Suitable thrombin inhibitors include hirudin, lepirudin, bivalirudin, argatroban, dabigatran, ximelagatran and combinations thereof.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

Materials and Methods

Medical-grade PTFE sheets with a thickness of 1 mm were purchased from Scientific Commodities Inc. All other chemicals were purchased from Sigma-Aldrich and used as received. DI water was used throughout the experiment.

PTFE Modification

PTFE sheets were first cleaned by ultrasonication in a 20% ethanol solution for 30 minutes. The PTFE sheets were then treated with oxygen plasma to enhance their surface hydrophobicity via a plasma etcher (PlasmaEtch PE-200) at an RF power of 200 W for 30 minutes at an oxygen flow rate of 20 $cm^3$/min. The plasma-treated PTFE sheet was named P-PTFE. P-PTFE was further coated with dopamine (DA) by immersing it into a 2 mg/mL dopamine solution with a pH of 8.5 adjusted by 10 mM tris(hydroxymethyl)aminomethane for 16 hours at room temperature. After coating, samples were rinsed with DI water 5 times and dried with nitrogen. Dopamine-coated P-PTFE sheets were named DA-PTFE. To further enhance the surface biocompatibility and anti-thrombogenic properties, RGD and heparin were chemically grafted onto DA-PTFE via a thin layer of PEI molecules. Briefly, PEI was dissolved in a citric acid/sodium phosphate dibasic buffer solution with a pH of 5.5 at a concentration of 0.5 mg/mL. DA-PTFE was immersed in the PEI solution for 1 hour at room temperature, then rinsed with DI water and dried using nitrogen. Another buffer solution containing 20 mM of EDC, 50 mM of NHS, and 0.1 M MES was prepared. An RGD solution (100 μg/mL) and an RGD/heparin solution (100 μg/mL for RGD and 1 mg/mL for heparin) were prepared using the above buffer. PEI-modified samples were soaked separately in these solutions overnight, followed by sufficient washing and drying, to prepare RGD-grafted PTFE, which was named RGD-PTFE, and RGD/heparin-grafted PTFE, which was named R/H-PTFE.

Characterization of Prepared PTFE Sheets

Fourier transform infrared (FTIR) spectra were recorded in transmittance mode to verify the modifications using a Bruker Tensor 27 spectrometer in the range of 4000-600 $cm^{-1}$, with a resolution of 4 $cm^{-1}$. X-ray photoelectron spectroscopy (XPS) measurements of different modified PTFE samples were performed on an X-ray photoelectron spectrometer with a focused, monochromatic K-alpha X-ray source and a monoatomic/cluster ion gun (Thermo Scientific). The C1s core-level signal spectra were Gaussian fitted and the proportion of each bond was determined from the peak area ratios. Scanning electron microscopy (SEM) was used to characterize the morphological properties. Samples were first coated with a thin layer of gold and then imaged using a fully digital LEO GEMINI 1530 SEM (Zeiss, Germany) at a voltage of 3 kV. The surface topography of different modified PTFE samples was analyzed using a Bruker BioScope Catalyst atomic force microscope (AFM) in tapping mode. The wettability of the modified PTFE samples was measured by a video contact angle instrument (Dataphysics, OCA 15) using 7 μL of DI water droplets with the sessile drop method.

Platelet Adhesion Test

Platelet adhesion tests were performed to investigate the antithrombogenicity of the modified PTFE sheets. Platelet-rich-plasma (PRP) was extracted from fresh human blood stabilized with 3.8% sodium citrate as an anticoagulant (Innovative Research). The blood was centrifuged at 1500 rpm for 15 minutes to obtain PRP. For the platelet adhesion test, samples were first incubated in phosphate-buffered saline (PBS) at 37° C. for 1 hour. Then, PBS was aspirated and 500 μL of PRP were added, followed by incubation at 37° C. for 2 hours. After incubation, samples were rinsed three times with PBS and treated with 2.5 wt % glutaraldehyde in PBS at 4° C. for 1 day. After that, samples were subjected to a series of ethanol solution washes (50%, 70%, 80%, 90%, and 100%) and dried in a desiccator overnight, followed by gold coating and imaging using SEM.

Human Umbilical Vein Endothelial Cell (HUVEC) Culture

Human umbilical vein endothelial cells (HUVECs; Lonza) were maintained on T75 tissue culture-treated polystyrene flasks. Cells were fed every other day with an endothelial cell growth medium EGM-2-MV bullet kit (Lonza). Prepared PTFE sheets were cut to the same size, put in 24-well tissue culture plates (TCPs), and washed in a 20% ethanol solution 5 times, followed by washing 3 times with PBS. They were then sterilized with ultraviolet (UV) light for 30 minutes. HUVECs were detached enzymatically with a trypsin-EDTA solution and seeded on the samples at a density of $1 \times 10^4$ cells/cm$^2$ for the live/dead assay and MTS assay. They were seeded at a density of $1 \times 10^3$ cells/cm$^2$ for the cytoskeleton assay. Spent medium was aspirated and replaced with 1 mL of fresh medium daily for screening samples. HUVECs were also cultured on TCPs as a control.

Biological Characterization

Initial cell attachment was evaluated at 4 hours after cell seeding. The cells were fixed in 4% paraformaldehyde for 15 minutes, followed by a PBS rinse, and then treated with 0.1% Triton-X in PBS for 5 minutes at room temperature. They were rinsed again with PBS and stained with 3 μM 4',6-diamidino-2-phenylindole (DAPI) for 1 hour at room temperature. Samples were then rinsed with PBS and imaged using a Nikon Eclipse Ti-E inverted fluorescence microscope.

Cell viability was determined after culturing for 7 days and 14 days. Viability was assessed via a live/dead viability/cytotoxicity kit (Life Technologies). Green fluorescent calcein-AM was used to target the esterase activity within the cytoplasm of living cells, while the red fluorescence ethidium homodimer-1 (EthD-1) was used to indicate cell death. Stained cells were imaged with a Nikon A1RSi inverted confocal microscope system. The number of collected cells that fluoresced red and green were counted with an Accuri C6 (BD Biosciences) flow cytometer to obtain viability data. Briefly, the stained cells of the live/dead assay were detached from the scaffolds by incubation in 250 μL of trypsin (Life Technologies) per well at 37° C. for 5 minutes. Then the cells were collected and centrifuged at 1000 rpm for 5 minutes. Next, the supernatant was aspirated and the cells were resuspended in 600 μL of PBS and filtered prior to analysis.

Cell proliferation was assessed at day 7 and day 14 by MTS assay using the CellTiter 96 Aqueous One Solution kit (Promega Life Sciences). Cells were first treated with media containing a 20% MTS solution and allowed to incubate for 1 hour. After incubation, 100 μL of spent media were transferred into a clear 96-well plate. The absorbance of the plates at the 450 nm wavelength was read with a Glomax-Multi+Multiplate Reader (Promega). The subsequent number of cells was determined relative to the negative control.

The shape and cytoskeleton organization of the cells were determined by phalloidin-tetramethylrhodamine B isothiocyanate (phalloidin-TMRho, Sigma) staining. For this assay, cells were first fixed following the same procedure in the cell attachment assay. They were then treated with 0.3 μM of phalloidin-TMRho with DAPI for 1 hour at room temperature. Next, samples were washed with PBS and imaged using the same confocal microscope.

The interaction between cells and substrate was observed using SEM. Briefly, the samples stained with phalloidin/DAPI were dehydrated through a series of ethanol solution (50%, 70%, 80%, 90%, and 100%) washes and sufficiently dried in a desiccator. They were then coated with gold and imaged using SEM.

Statistical Analysis

All biological results are presented as mean±standard deviation. All of the values were averaged at least in triplicate. The data were analyzed using the one-way analysis of variance method (ANOVA). The Tukey's test was then used to evaluate the specific differences of the data, and these differences were considered statistically significant at $p<0.05$.

Results and Discussion

Figure 2:
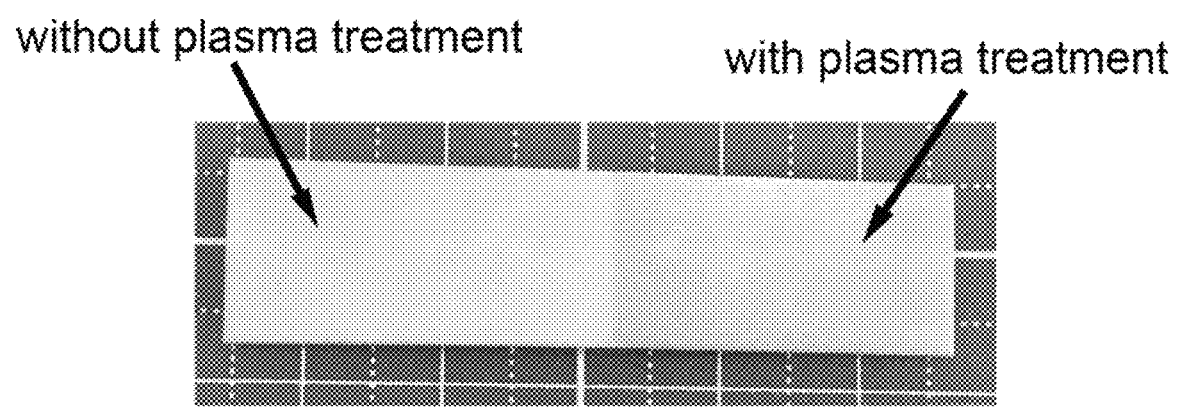
FIG. 2 depicts a digital photo of a dopamine-coated PTFE (DA-PTFE) sheet. The left part was protected with tape during the $O_2$ plasma treatment.

A series of surface modifications were carried out on flat PTFE sheets as shown in FIG. 1. The effect of each modification on the cellular substrate interaction was determined to enhance the bioactivity of hydrophobic surfaces. Oxygen plasma was first used to introduce hydrophilic groups on the PTFE surface prior to dopamine (DA) coating. Although it has been reported that dopamine is able to coat any surface, regardless of hydrophobicity, its coating efficiency was greatly improved when the PTFE was first treated with $O_2$ plasma. As evidenced in FIG. 2, the plasma-treated PTFE showed a distinctly darker color than the PTFE without plasma treatment, thus indicating that more dopamine was coated on the P-PTFE. To further graft bioactive molecules onto the substrate surface, a very thin layer of polyethylenimine (PEI) was immobilized on the polydopamine to introduce reactive amino groups on the substrate surface. The PEI concentration was controlled at a low level (0.5 mg/mL) to improve cell adhesion and avoid cell death caused by an excess amount of PEI. Chemical grafting of RGD or RGD/heparin was performed using EDC/NHS grafting chemistry. In this grafting process, carboxyl groups on RGD and heparin were reacted while the bioactive component of RGD and the antithrombotic sulfo group of heparin were preserved and exposed on the substrate surface.

Figure 3:
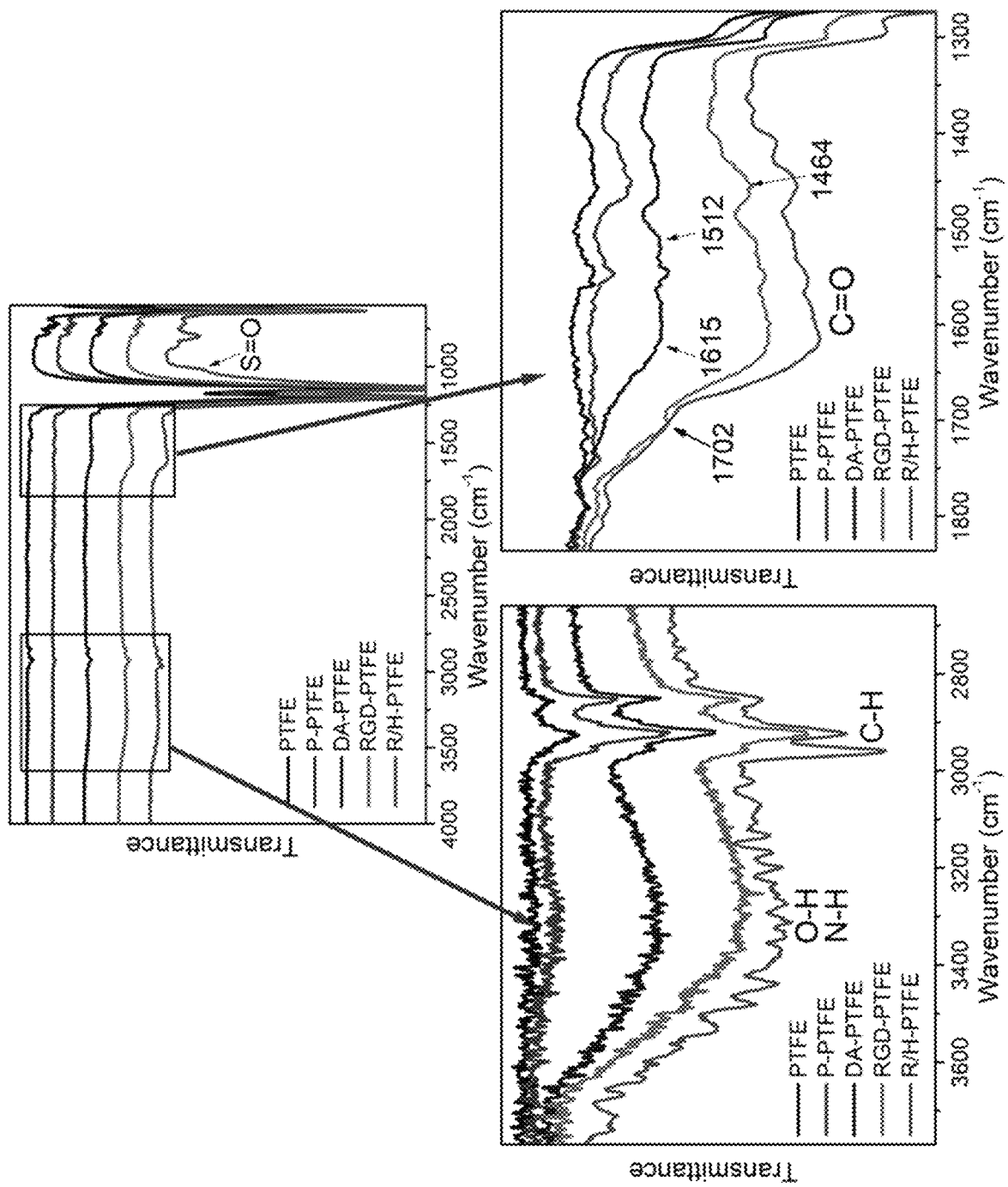
FIG. 3 depicts FTIR spectra of PTFE, P-PTFE, DA-PTFE, RGD-PTFE, and R/H-PTFE. Two regions are enlarged for better comparison.

The chemical composition of the modified PTFE sheets was first characterized using FTIR. As shown in FIG. 3, all materials showed very similar peak patterns due to the strong signal from the PTFE substrate. However, the difference among samples can be seen when specific regions are enlarged. The plasma-treated PTFE (P-PTFE) showed the same peak pattern as PTFE, except for a small wide peak at 3300 $cm^{-1}$ indicating the introduction of a small amount of hydroxyl groups. The intensity of this peak significantly increased after dopamine coating due to the O—H and N—H bonds of polydopamine. Moreover, another peak attributed to C=O presented at 1615 $cm^{-1}$, and the peak for C=N and C=C was also observed at 1512 $cm^{-1}$. These results indicated the successful coating of dopamine on the substrate surface. The RGD-grafted PTFE showed more intense peaks in the enlarged regions. The increase of the peak at 3300 $cm^{-1}$ was attributed to the N—H from PEI and RGD. The peaks at 1702 $cm^{-1}$ and 1464 $cm^{-1}$ corresponded to the amide I and III of RGD. Interestingly, the wavenumbers of these peaks shifted higher compared to the freeze-dried RGD from the references. This might have been due to the formation of hydrogen bonds with dopamine, which would further immobilize the RGD on the substrate surface. When heparin was further grafted onto the PTFE surface, a shoulder peak assigned to S=O asymmetry vibration presented on the FTIR spectrum at 1018 $cm^{-1}$. Additionally, the intensity of the C=O peak at 1615 $cm^{-1}$, and the peak at 3300 $cm^{-1}$, increased, thus indicating the successful grafting of heparin.

Figure 4:
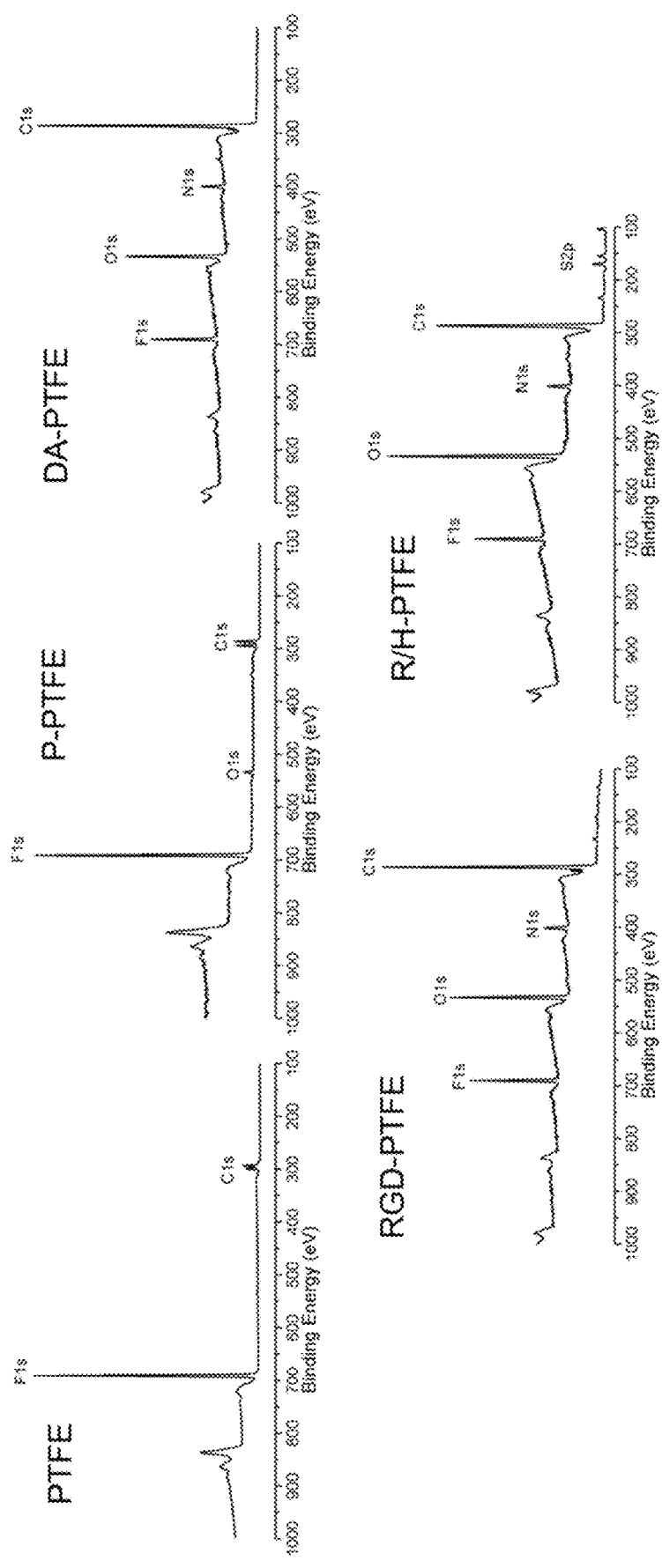
FIG. 4 depicts XPS survey scans of PTFE, P-PTFE, DA-PTFE, RGD-PTFE, and R/H-PTFE.
Figure 5:
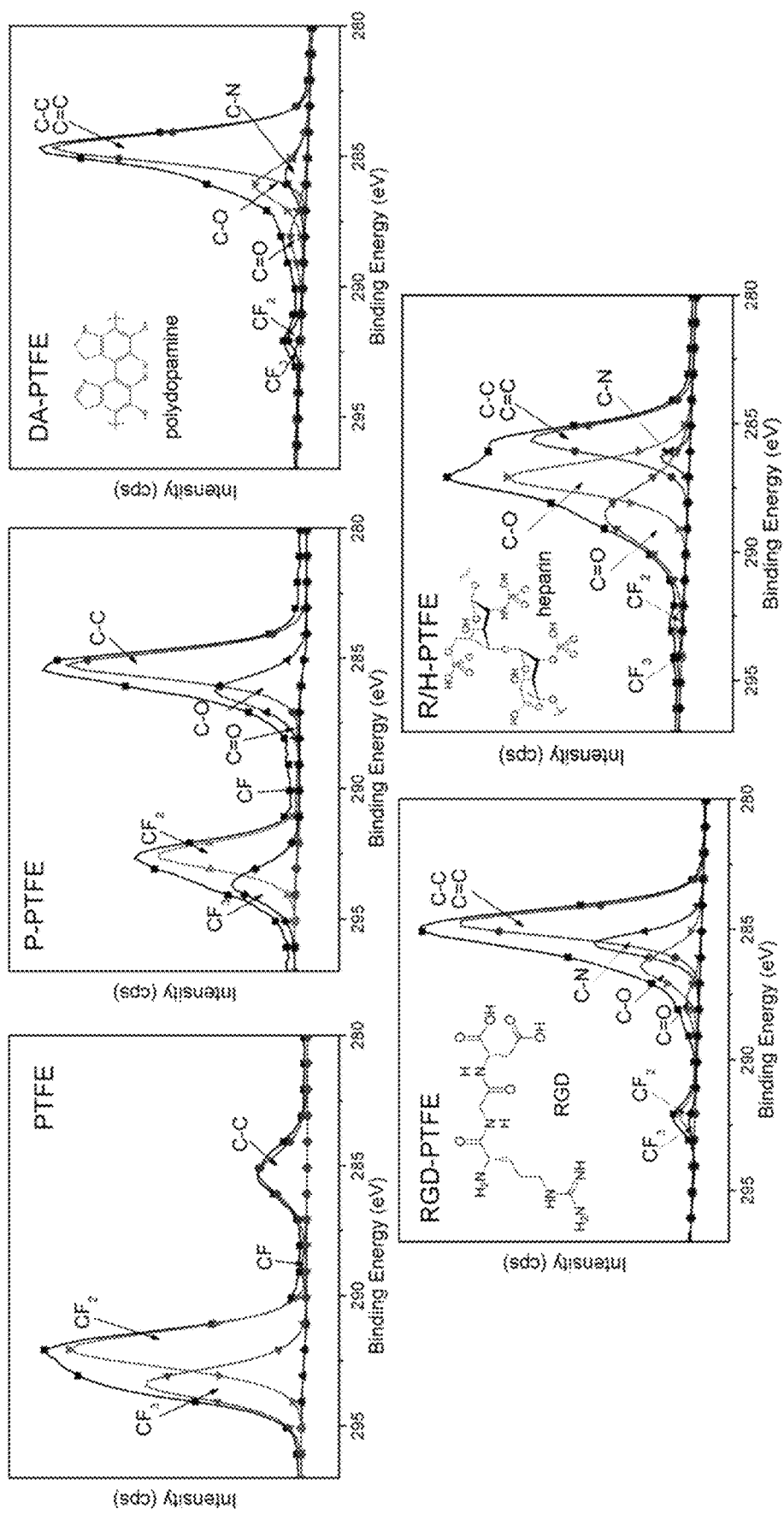
FIG. 5 depicts Gauss-fitted C1s high-resolution scans of PTFE, P-PTFE, DA-PTFE, RGD-PTFE, and R/H-PTFE showing the composition of different carbon bonds. The insets show the chemical structure of polydopamine, RGD, and heparin.

Since the strong signal from PTFE in the FTIR measurements may hide some details in the surface chemistry, XPS was used to further characterize the surface layer of the modified samples. From the survey scans (FIG. 4) and atom percentage statistical data (Table 1), it was found that only C and F were detected on PTFE, while 4.1% O was detected on P-PTFE, thus indicating the introduction of hydrophilic groups. Nitrogen was detected on the surface of DA-PTFE and RGD-PTFE at a rate of 5.5% and 8.2%, respectively, suggesting the introduction of bioactive components. On the R/H-PTFE, 2.1% of S was detected, which confirmed the grafting of heparin. The C1s core level scans show the detailed information of carbon-containing bonds on the material surface (FIG. 5). According to statistical data (Table 2), the proportion of $CF_2$ and $CF_3$ was reduced by more than half after plasma treatment, and it was less than 5% after dopamine coating, thus suggesting an increase in surface energy. As expected, C—O, C=O, and C—N bonds were present on DA-PTFE, and the proportion of C—N bonds greatly increased after RGD grafting, which was attributed to the massive amide bonds on RGD. Similarly, C—O bonds dominated when heparin was grafted, which corresponded to the increase in C—O—C linkages from heparin. Therefore, the XPS results further confirmed the success of each modification step. The surface chemistry of PTFE was tuned by dopamine coating and RGD or RGD/heparin grafting.

TABLE 1

Atom percentage results of PTFE, P-PTFE, DA-PTFE, RGD-PTFE, and R/H-PTFE from XPS survey scans.

| Atom | PTFE | P-PTFE | DA-PTFE | RGD-PTFE | R/H-PTFE |
|---|---|---|---|---|---|
| C | 33.7 | 36.7 | 69.9 | 65.1 | 60.9 |
| O | 0.1 | 4.1 | 15.3 | 17.3 | 24.2 |
| F | 66.2 | 59.2 | 9.3 | 9.4 | 7.3 |
| N | / | / | 5.5 | 8.2 | 5.5 |
| S | / | / | / | / | 2.1 |

TABLE 2

XPS C1s core-level scans of PTFE, P-PTFE, DA-PTFE, RGD-PTFE, and R/H-PTFE showing the binding energy (BE) and percentage of different carbon containing bonds.

| Element | PTFE BE | PTFE % | P-PTFE BE | P-PTFE % | DA-PTFE BE | DA-PTFE % | RGD-PTFE BE | RGD-PTFE % | R/H-PTFE BE | R/H-PTFE % |
|---|---|---|---|---|---|---|---|---|---|---|
| C—C, C=C | 286.3 | 13.4 | 286.3 | 42.7 | 284.7 | 65.0 | 284.8 | 55 | 285.6 | 30.4 |
| C—N | / | / | / | / | 285.7 | 8.0 | 285.6 | 20.6 | 286.4 | 2.8 |
| C—O | / | / | 286.3 | 17.3 | 286.1 | 17.4 | 286.4 | 16.3 | 287.1 | 35.7 |
| C=O | / | / | 287.8 | 0.8 | 287.9 | 6.3 | 287.8 | 4.0 | 288.5 | 29.3 |
| CF | 289.9 | 1.0 | 289.2 | 0.1 | / | / | / | / | / | / |
| $CF_2$ | 293.1 | 52.9 | 292.6 | 25.2 | 292.0 | 2.7 | 292.1 | 3.0 | 292.8 | 1.2 |
| $CF_3$ | 294.4 | 32.7 | 293.7 | 13.9 | 292.5 | 0.7 | 292.4 | 1.1 | 294.2 | 0.6 |

Figure 6:
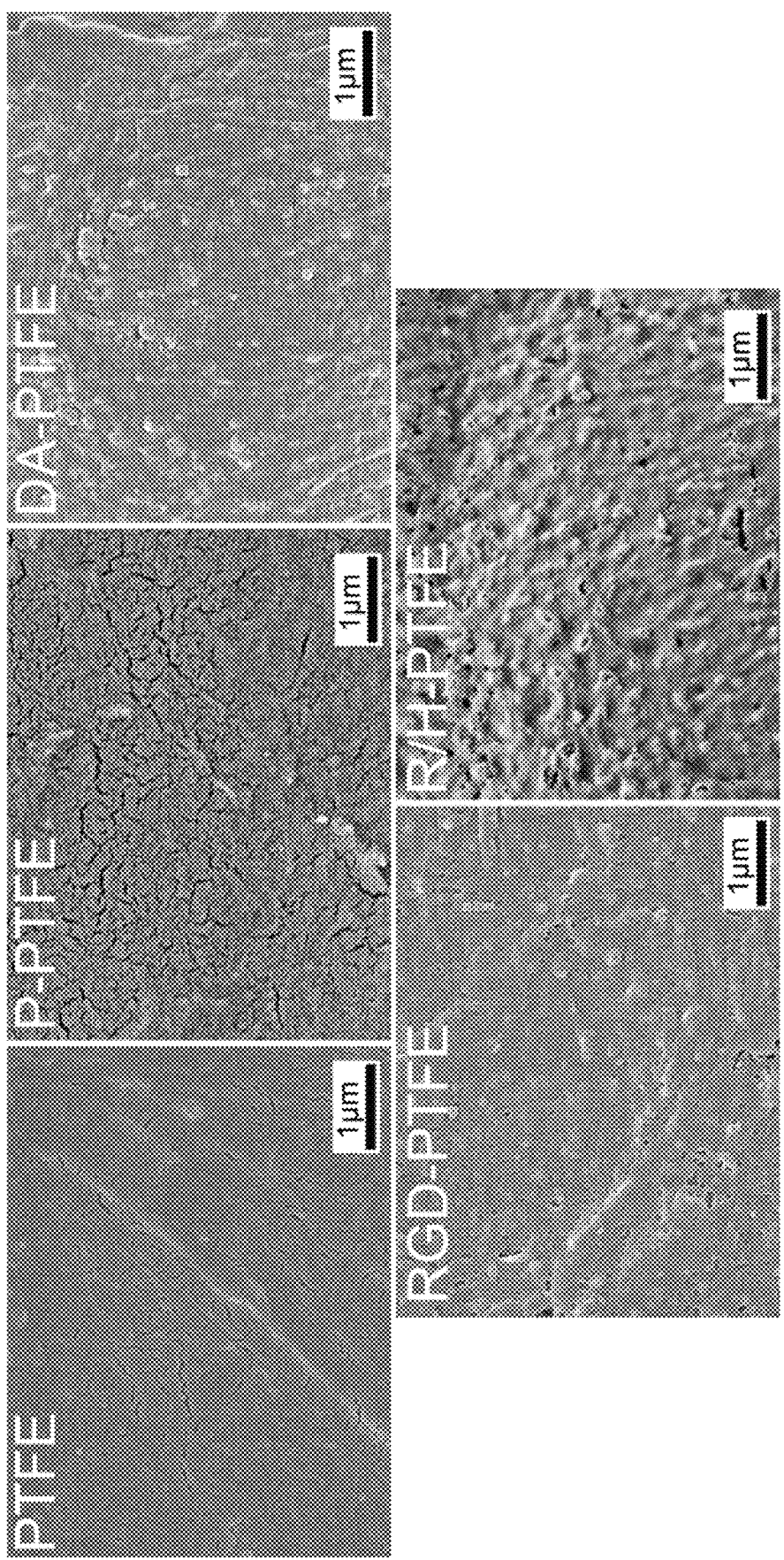
FIG. 6 depicts SEM images of the surface morphologies of PTFE, P-PTFE, DA-PTFE, RGD-PTFE, and R/H-PTFE samples.

The surface morphology of modified PTFE sheets was imaged using SEM. As can be seen from FIG. 6, neat PTFE showed a relatively smooth surface. After 30 minutes of $O_2$ plasma treatment, some cracks showed on the P-PTFE surface, indicating the cleavage of carbon bonds. Dopamine-coated PTFE (DA-PTFE) showed a coating layer with increased surface roughness. It has been reported that self-polymerized polydopamine forms nanoparticles in an aqueous solution. When coated on PTFE, these particles merged to form a film, but some particulate morphology was still observable on the material surface. When RGD was grafted on DA-PTFE with the PEI layer, the surface morphology of RGD-PTFE remained about the same. Remarkably, when heparin was grafted on the surface, R/H-PTFE showed a much rougher surface with many nanoparticles (~50 nm) anchored to the substrate surface. This was because heparin molecules tend to aggregate and form nanoparticles when dried from an aqueous solution. A similar rough surface was also found when heparin was directly coated onto a poly (lactic acid) (PLA) membrane.

Figure 7:
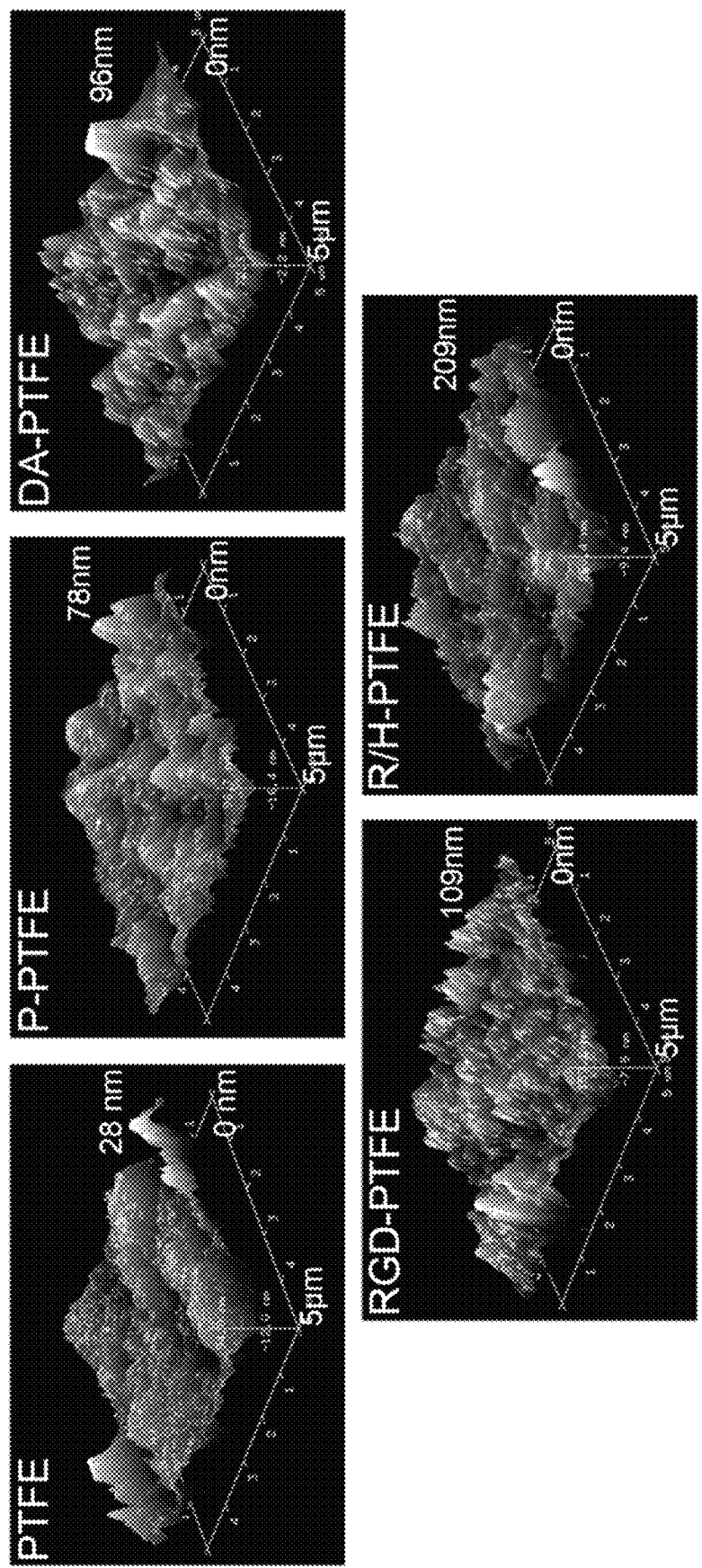
FIG. 7 depicts three-dimensional AFM images of PTFE, P-PTFE, DA-PTFE, RGD-PTFE, and R/H-PTFE across a 5 μm×5 μm area. The height differences are marked on the images.
Figure 8:
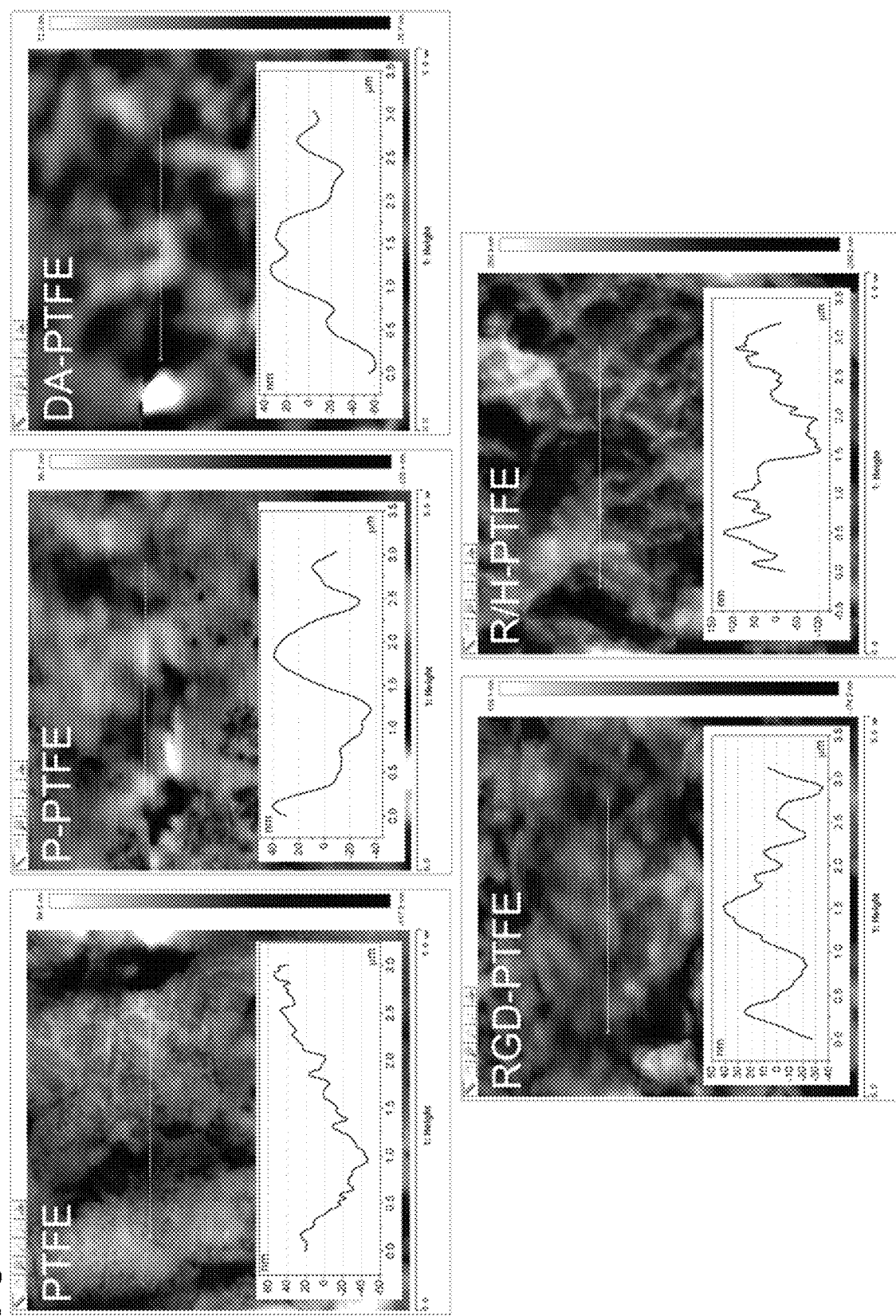
FIG. 8 depicts cross-sectional AFM images corresponding height profiles from the lines drawn on each image from FIG. 7.

The surface topography of modified PTFE sheets was further characterized using AFM to quantify the change of surface roughness in each modification step. As shown in the 3D AFM images (FIG. 7) and cross-sectional images (FIG. 8), PTFE showed a height difference of 28 nm. The micro grooves observed in the images were caused by the finishing of the pristine PTFE sheets during production. After $O_2$ plasma treatment, the height difference increased to 78 nm, thus indicating that some PTFE had been etched away. A greater increase in height difference (from 18 nm to 135 nm) is observed when PTFE sheets are treated with $N_2$ plasma for 3 hours. The height difference further increased after dopamine coating and RGD grafting as shown in FIG. 7. Notably, after grafting with RGD and heparin, the height difference increased to 209 nm, which was significantly higher than other samples. This was because of the nanoparticles formed by heparin and was in agreement with SEM observations. The increased surface roughness should be favorable for cell attachment since rough surfaces have been found to facilitate serum protein adsorption and enhance osteoblast cell adhesion.

Figure 9A:
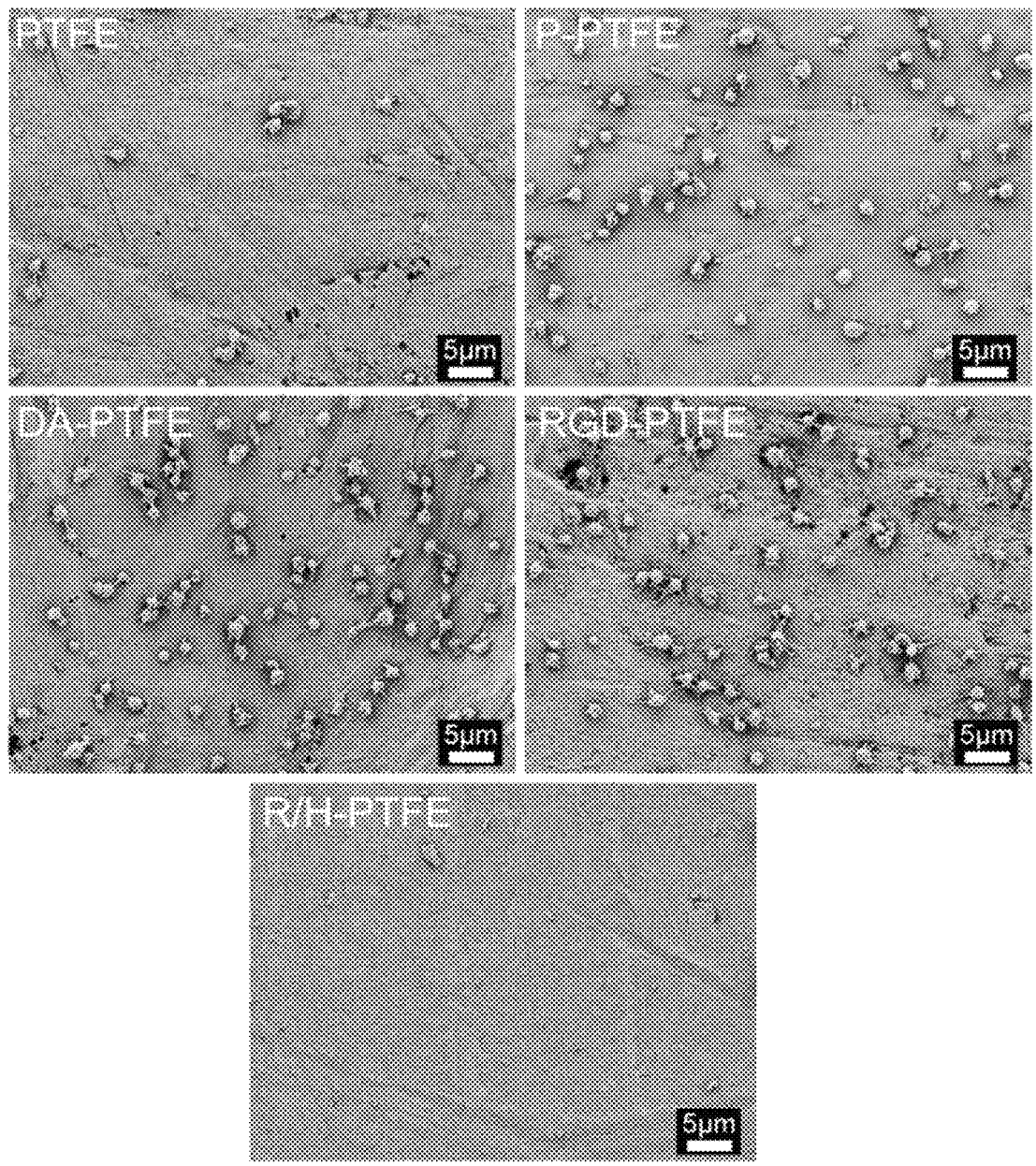
FIGS. 9A-9C depict SEM images of platelets attached to PTFE, P-PTFE, DA-PTFE, RGD-PTFE, and R/H-PTFE (FIG. 9A), statistical results of the platelet adhesion test (FIG. 9B), and water contact angle results of different PTFE samples (FIG. 9C).
Figure 9B:
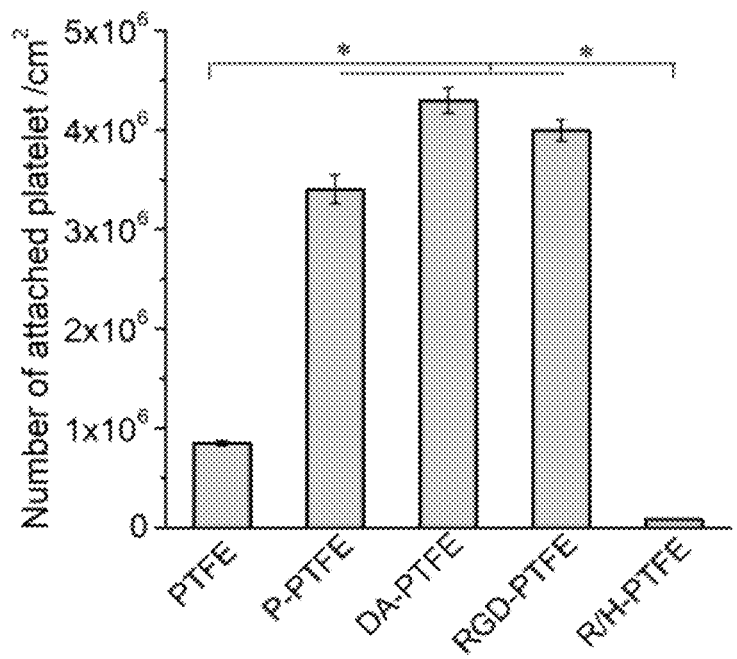
Figure 9C:
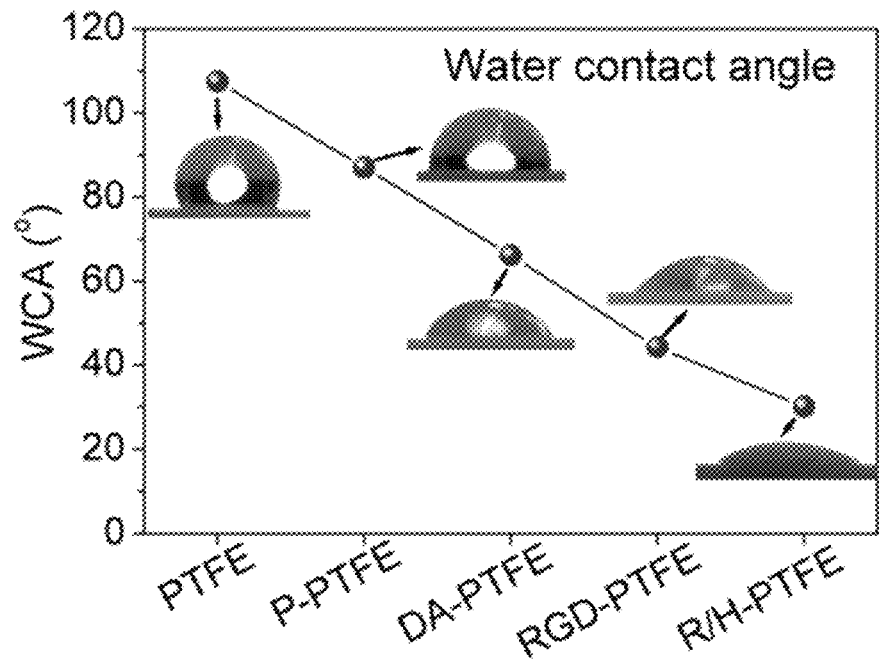

A great challenge for vascular grafts is the risk of thrombosis due to the coagulation of platelets. Platelet adhesion was evaluated to understand the effect of surface modification on the risk of thrombosis. As shown in FIG. 9A, the platelets adhered on the substrate had round shapes indicating that they generally had a low attachment force to the substrate. The number of attached platelets on P-PTFE, DA-PTFE, and RGD-PTFE was significantly higher than on PTFE and R/H-PTFE as shown in the statistical results (FIG. 9B). Remarkably, almost no platelets adhered to R/H-PTFE. Without being bound by theory, it is believed that the lower platelet adhesion for PTFE was associated with its low surface roughness and high hydrophobicity. As shown in the water contact angle (WCA) measurements (FIG. 9A), the WCA decreased after each modification step because more hydrophilic components were introduced in each step. The surface roughness, on the contrary, gradually increased as demonstrated above. The combination of these two factors caused increased platelet adhesion after modification. However, R/H-PTFE showed very low platelet adhesion although it possessed the lowest WCA and highest surface roughness.

Figure 10:
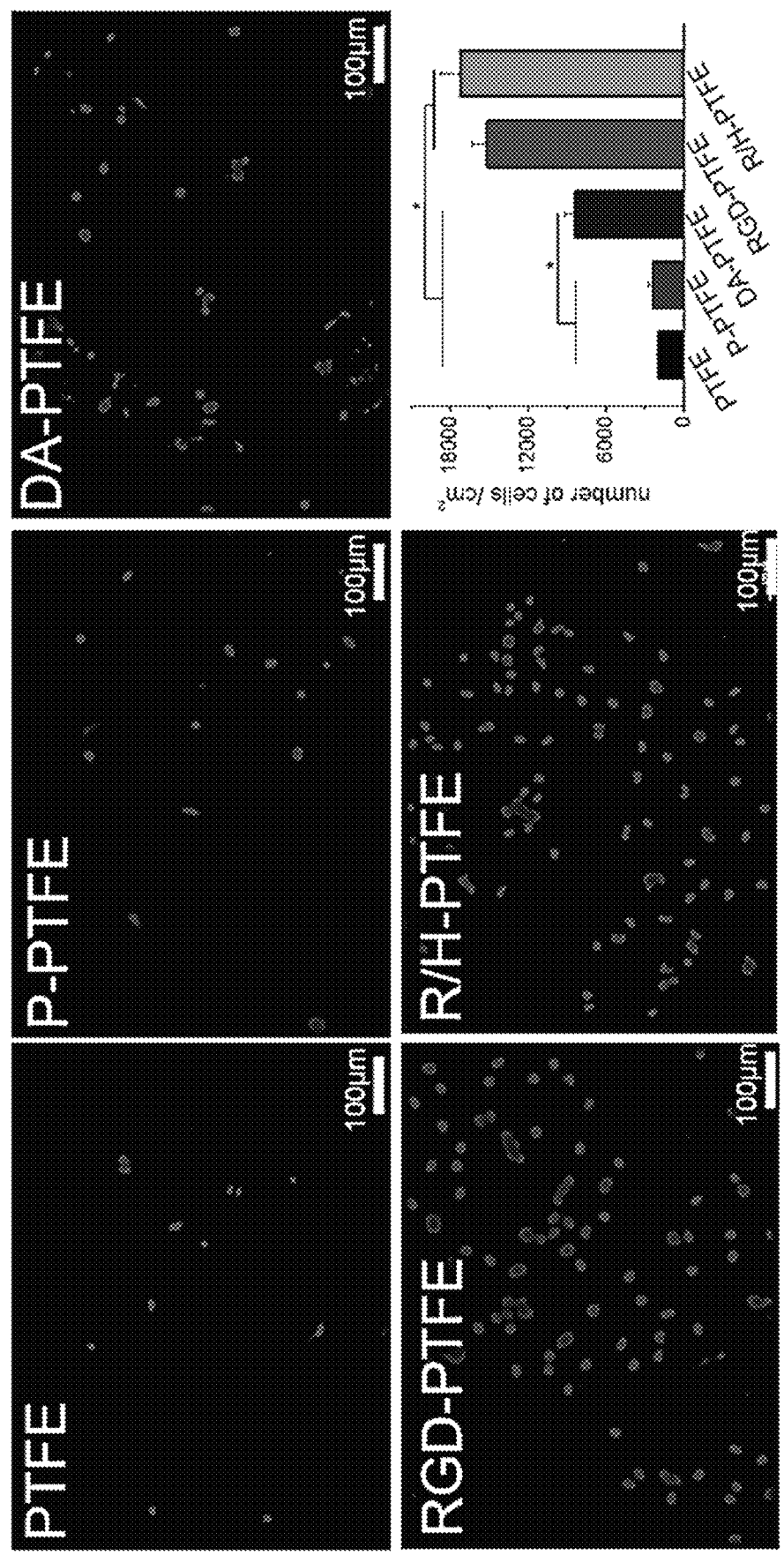
FIG. 10 depicts HUVEC attachment results after cell seeding for 4 hours. Cell nuclei were stained with DAPI. The lower right diagram shows the statistical results of the number of cells attached to the different substrates.

To investigate the effect of different modifications on cellular-substrate interactions, HUVECs were cultured on pristine PTFE and different PTFE samples. Initial cell attachment was evaluated 4 hours after cell seeding. It was found that the cell attachment on PTFE and P-PTFE samples was significantly lower than on other samples. The dopamine-coated substrate showed improved cell adhesion. The samples grafted with RGD and RGD/heparin had significantly higher cell seeding than the one coated only with dopamine (FIG. 10).

Figure 11A:
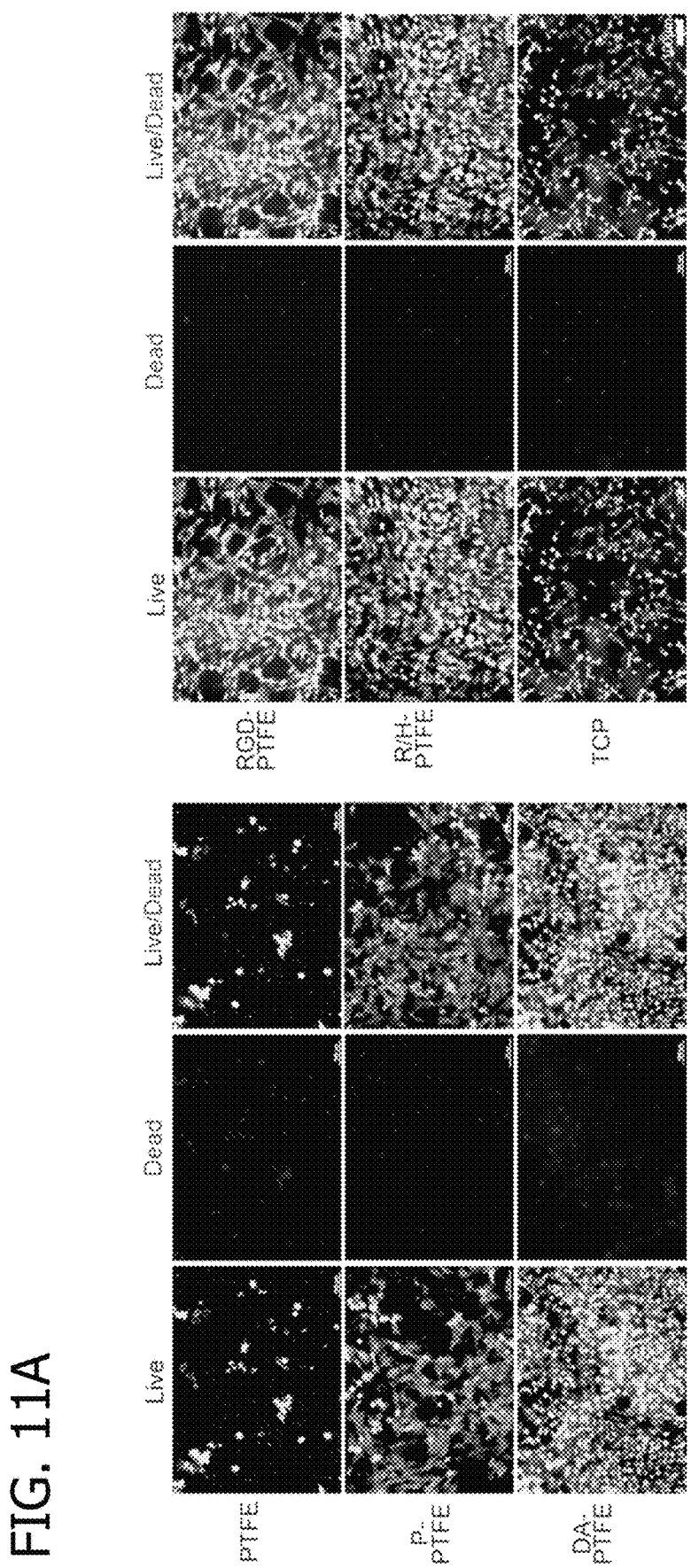
FIGS. 11A-11C depict fluorescent images of HUVECs cultured on different PTFE substrates for 7 days (FIG. 11A), statistical results of cell viability from live/dead assay (FIG. 11B), and statistical results of cell proliferation from MTS assay at day 7 and day 14 time points (FIG. 11C).
Figure 11B:
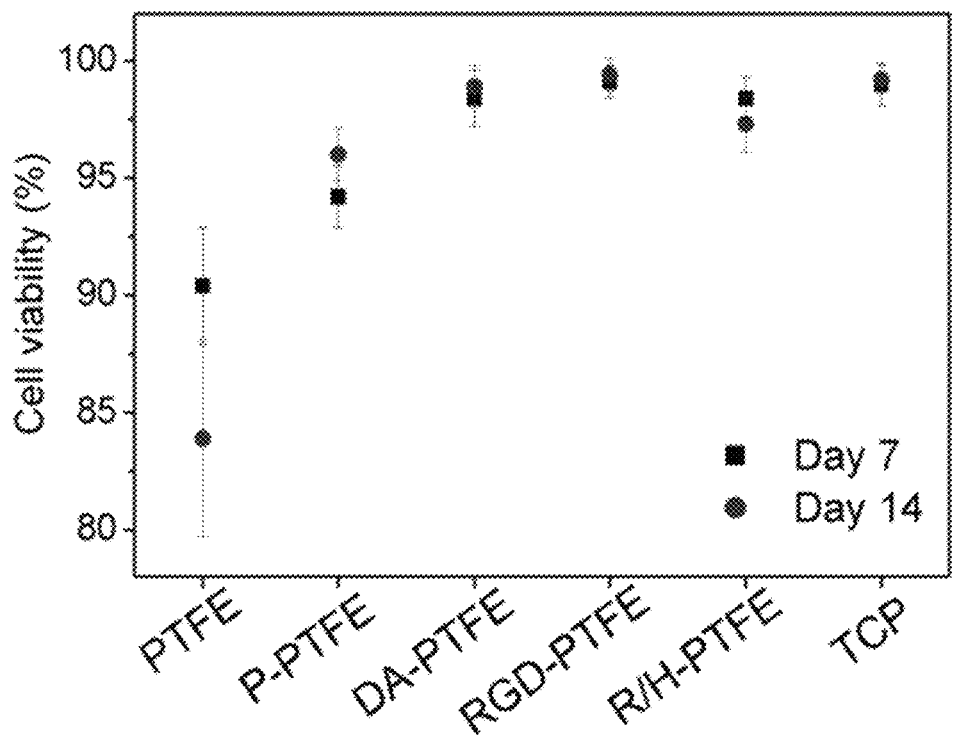
Figure 11C:
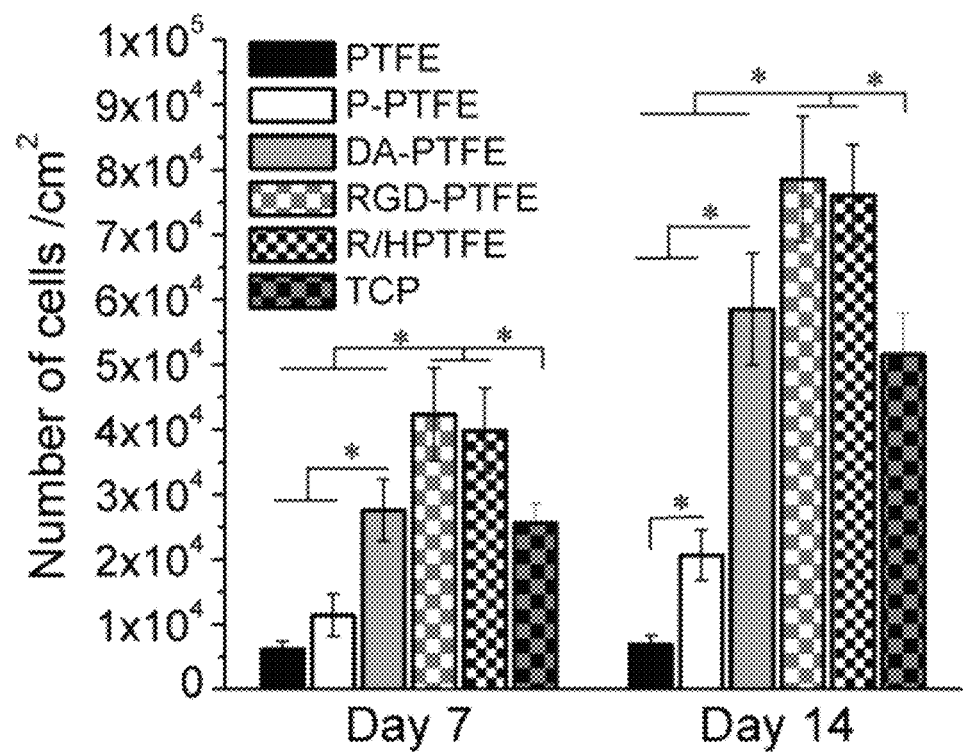
Figure 12:
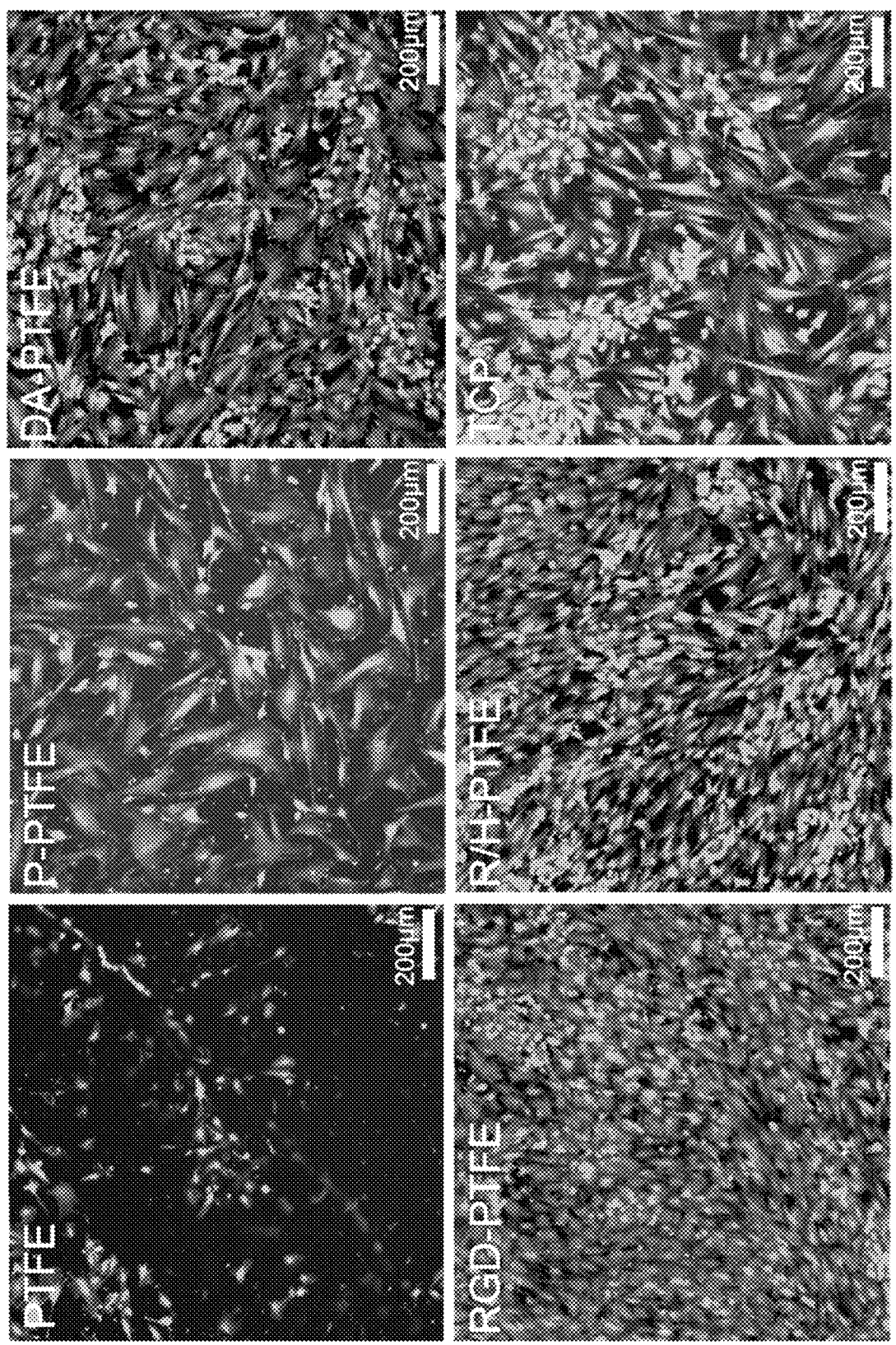
FIG. 12 depicts fluorescent images of HUVECs cultured on different PTFE substrates for 14 days. Bar=200 μm.

The viability of HUVECs on different modified PTFE substrates was investigated using a live/dead assay. The assay uses calcein-AM to stain live cells with green fluorescence and EthD-1 to target dead cells with red fluorescence. The fluorescence images showed that HUVECs were able to grow on all substrates (FIGS. 11A and 12), while the percentage of live cells (FIG. 11B) and the number of cells (FIG. 11C) differed among them. The results indicated that neat PTFE had a very low cell viability (FIG. 11B) and cell population (FIG. 11C) at both day 7 and day 14 time points, indicating that cells were not able to proliferate or proliferated slowly on PTFE. After $O_2$ plasma treatment, P-PTFE showed improved cell proliferation and viability at both time points. A significant improvement was achieved when PTFE was coated with dopamine. Compared to PTFE, DA-PTFE showed 4.5 times the cell population of PTFE at day 7, and it further increased to 8.4 times as many on day 14. When RGD or RGD/heparin was grafted, the cell proliferation improved further. Remarkably, at day 14, the number of cells on RGD-PTFE was 11 times that of PTFE, and it was also significantly higher than DA-PTFE and TCP. However, the difference between RGD-PTFE and R/H-PTFE was not significant, suggesting that RGD was the main cause of the increased cell affinity. This trend was maintained at both day 7 and day 14 time points and was consistent with the cell attachment results, which indicated that dopamine and RGD were able to not only facilitate initial cell attachment, but also stimulate cell growth over time. In addition, it was observed that HUVECs cultured on RGD-PTFE and R/H-PTFE showed smaller sizes than cells cultured on other samples (FIG. 11A). This was because of the significant increase in the cell population over the limited sample area. At day 14, the HUVECs cultured on DA-PTFE and TCP also became smaller compared to day 7 (FIG. 12).

Figure 13A:
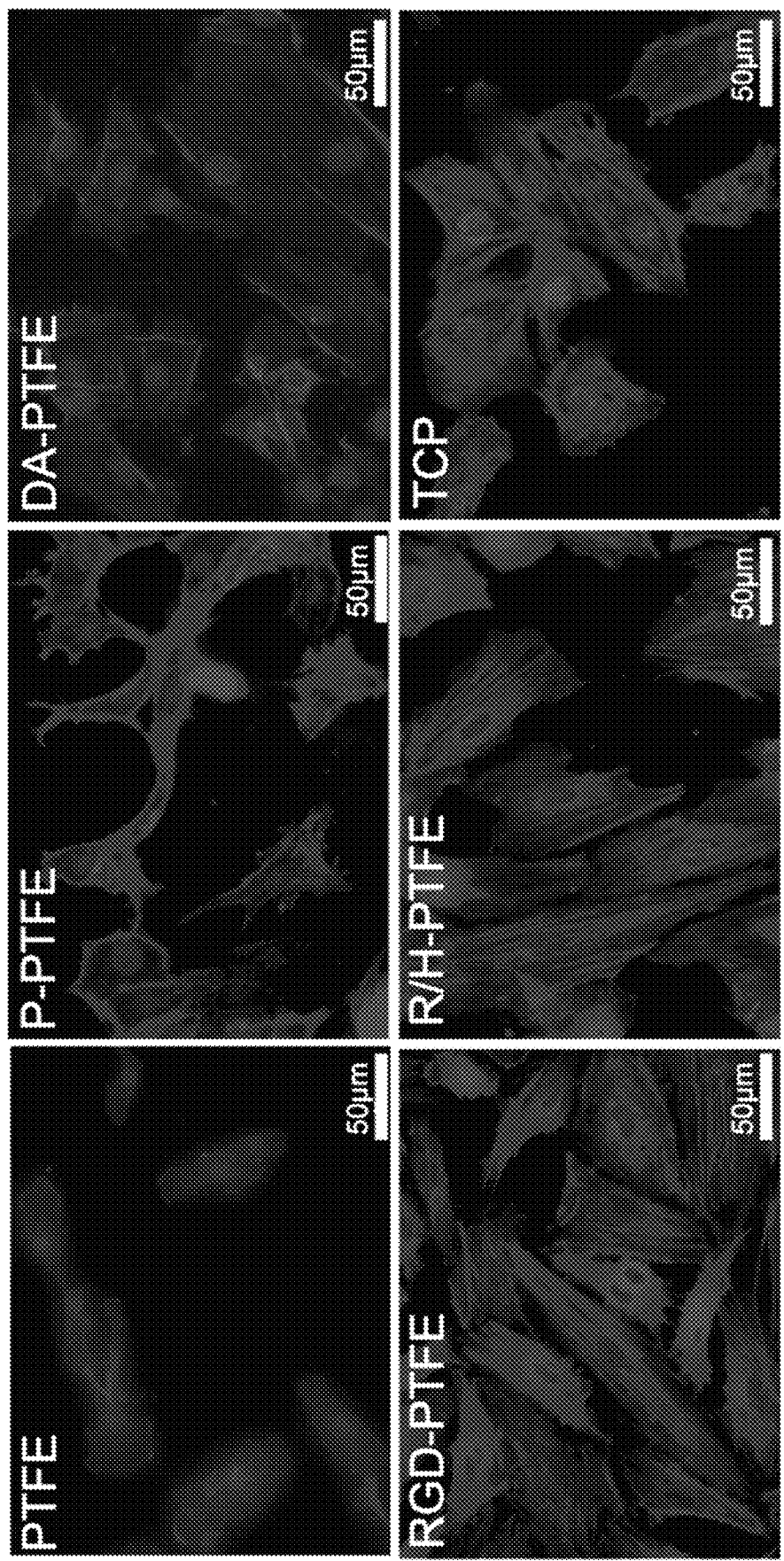
FIGS. 13A-13C depict fluorescent images showing the cytoskeleton of HUVECs cultured on different PTFE substrates for 7 days (FIG. 13A), measurement results of the average projected area per cell (FIG. 13B), and the average aspect ratio per cell (FIG. 13C).
Figures 13B, 13C:
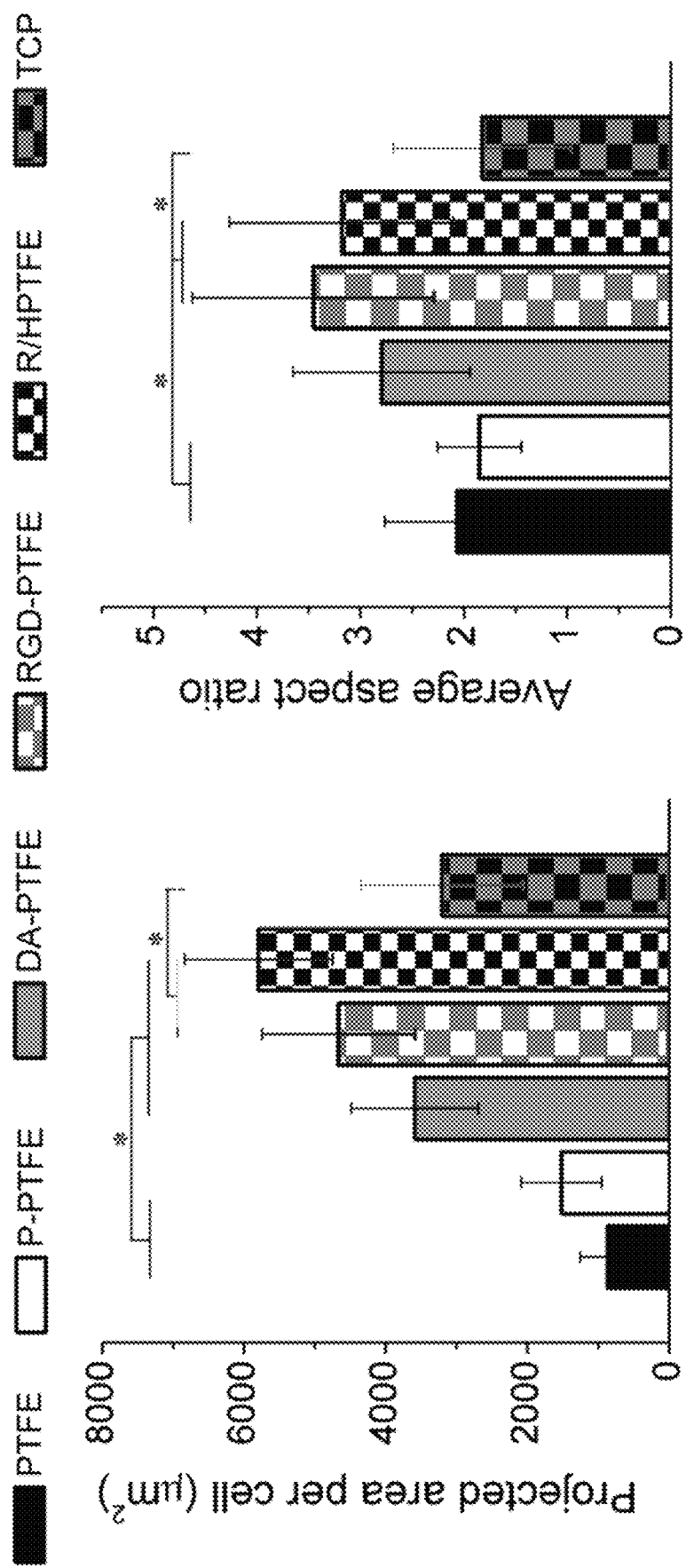
Figure 14:
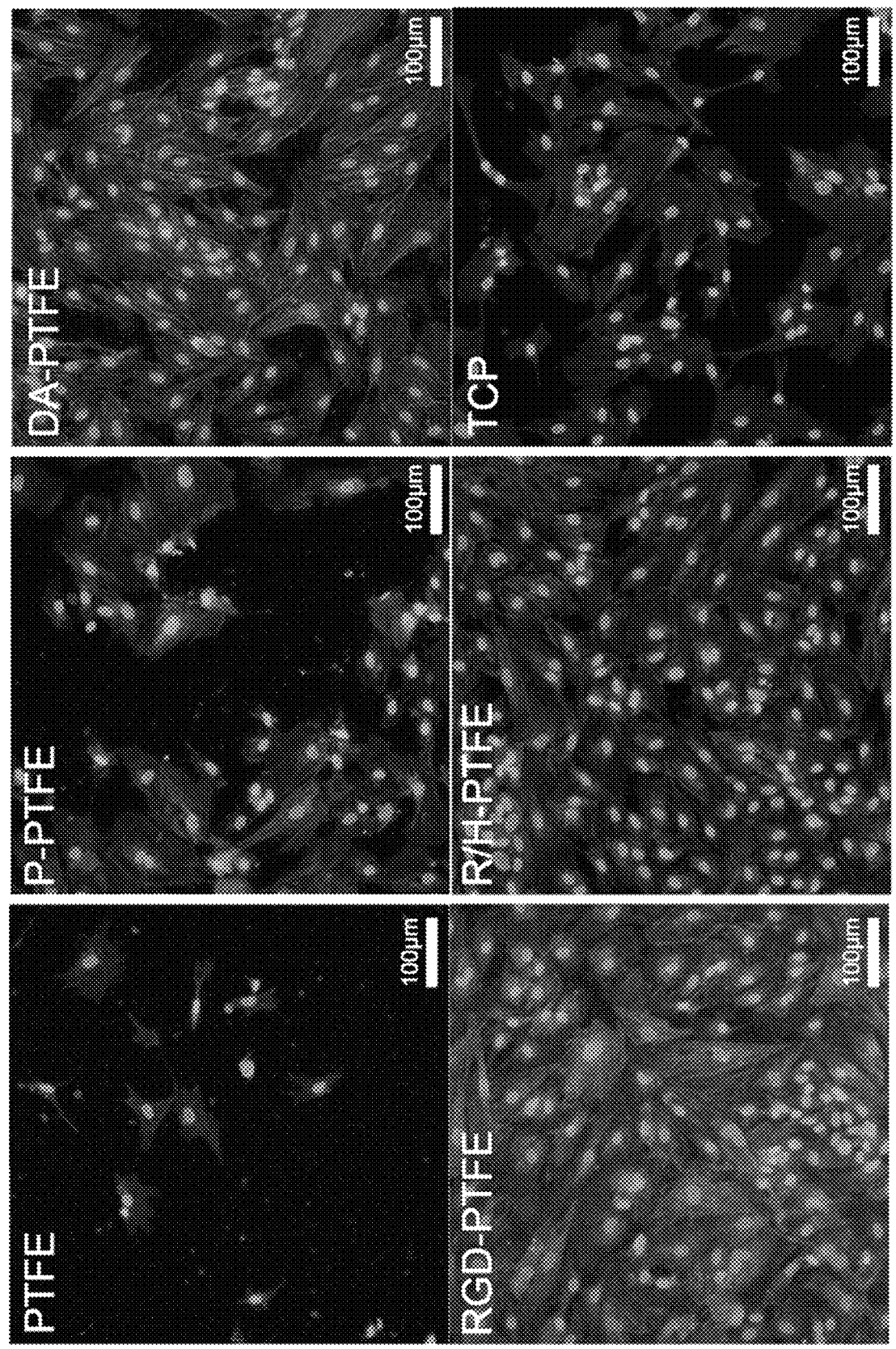
FIG. 14 depicts fluorescence images showing the cytoskeleton of HUVECs cultured on different PTFE substrates for 14 days.

To investigate cell phenotype, HUVECs were seeded on different PTFE substrates at a low density (5000 cells/well) and cultured for 14 days. The cytoskeletons of the cells were stained red with phalloidin-TMRho and cell nuclei were stained blue with DAPI. FIG. 13A shows the cytoskeleton of HUVECs cultured on different PTFE substrates for 7 days. As can be seen, both cell size and nuclei size of HUVECs cultured on PTFE were smaller than cells on other samples. The cells were not spread out and the fluorescence intensity was weak, thus indicating that cells did not show a healthy growing state. After a series of modifications, the cellular-substrate interaction greatly improved. For statistical comparison, the average projected cell area and aspect ratio of the cells were measured as shown in FIGS. 13B and 13C. It was found that samples with DA, RGD, and RGD/heparin modification showed significantly larger cell sizes than cells on PTFE and P-PTFE, and the cells were more spread out and stretched on those samples. Notably, the cells on RGD-PTFE and R/H-PTFE showed extremely flourishing growing states with a typical spindle-like cell morphology and filopodia. The average aspect ratio of the cells on RGD-PTFE and R/H-PTFE was over 3, which was significantly larger than those grown on PTFE and TCP (FIG. 13C). Moreover, the filaments in the cells can be clearly seen on cells grown on RGD-PTFE and R/H-PTE, thus indicating highly extended cell morphology. After 14 days of cell culture, the number of cells greatly increased on the DA-PTFE, RGD-PTFE, and R/H-PTFE samples (FIG. 14). In some regions of the RGD-PTFE and R/H-PTFE samples, cells started to grow on top of each other to form dense cell aggregates. Similar to the live/dead assay, the cell size decreased at day 14 due to the great increase in the number of cells, thus the projected cell area was not measured at day 14. All of these results strongly suggest that dopamine coating and RGD and heparin grafting greatly improved the biocompatibility and endothelial cell affinity of PTFE.

Figure 15:
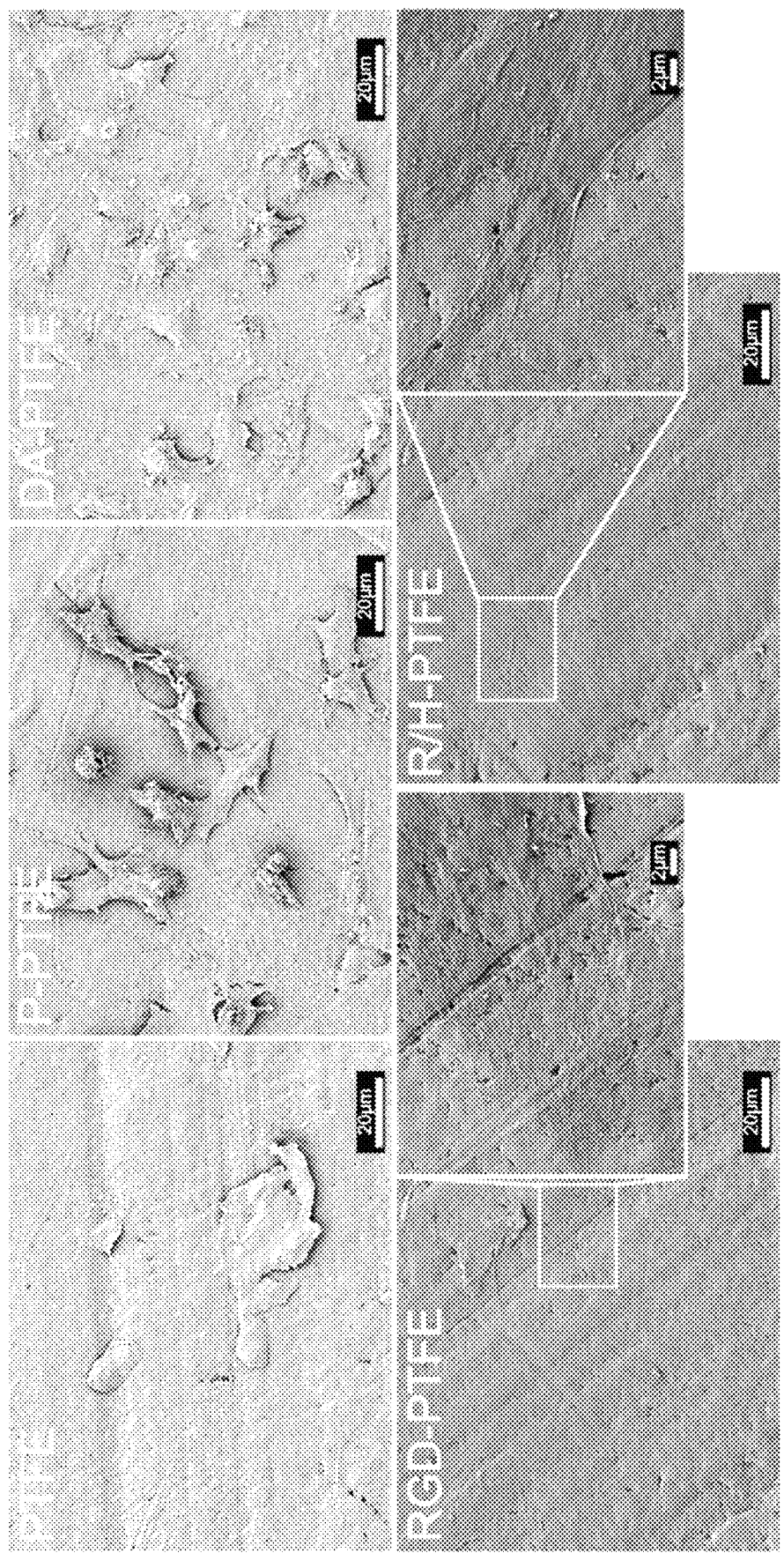
FIG. 15 depicts SEM images of HUVECs cultured on different PTFE substrates for 7 days showing the interaction between cells and substrate.

Samples at day 7 were imaged using SEM to observe the morphology of the cells on different substrates. As shown in FIG. 15, cells were rarely present on PTFE samples. Although more cells were observed on P-PTFE compared with PTFE, many of the cells were round and a gap was observed between the cells and the substrate, indicating poor cell adhesion. On the DA-PTFE sample, cells were flattened and showed tight adhesion to the substrate. Many cells were connected with each other by extended filopodia. Meanwhile, the cell boundaries were clearly seen and some cells observed were not fully spread. Remarkably, individual cells and cell boundaries were not observed at low magnification on the RGD-PTFE and R/H-PTFE samples. When observed under high magnification, cell membranes were greatly flattened and extended. For better observation, the cell membranes were highlighted in red on the enlarged SEM images in FIG. 15. The lamellipodia and filopodia were tightly attached to the substrate, and the boundary of the cell membrane was difficult to see, thus indicating strong cellular-substrate interaction.

The results demonstrate a facile modification method for the functionalization of PTFE with bioactive molecules such as dopamine (DA), RGD, and heparin towards their application as vascular grafts. Oxygen plasma treatment activated hydrophilic groups on PTFE's surface and facilitated dopamine coating. RGD and heparin were immobilized on DA-PTFE through a thin PEI layer. Successful modification in each step was verified via FTIR and XPS. The surface roughness increased as more components were grafted onto the PTFE surface, and the hydrophilicity increased due to the increased number of hydrophilic groups. Platelet adhesion increased after dopamine and RGD modification, but was decreased dramatically by grafting heparin onto the surface, thereby demonstrating excellent antithrombogenicity. In vitro, HUVEC cultures revealed that all of the modifications had a positive effect on the biocompatibility of PTFE. The initial cell attachment, cell viability, and cell proliferation all improved significantly when dopamine and RGD were grafted onto the PTFE surface, and the incorporation of RGD outperformed dopamine coating alone. Endothelial cells cultured on RGD- and RGD/heparin-grafted PTFE substrates exhibited favorable cell morphologies and strong cell-substrate interactions owing to the significantly enhanced cell affinity. Therefore, the methods described in the present disclosure provide simultaneous improvement of endothelial cell affinity and antithrombogenicity of hydrophobic surfaces. The method advantageously is highly suitable for the modification of SDVGs to stimulate fast endothelialization and effective antithrombosis.

What is claimed is:

1. A modified hydrophobic substrate comprising a substrate comprising a hydrophobic surface, a first layer comprising dopamine disposed on the hydrophobic surface, a second layer comprising a polymer comprising a terminal amine disposed on the first layer, and a third layer comprising at least one biomolecule covalently bonded to the terminal amine of the polymer of the second layer, wherein the at least one biomolecule is selected from the group consisting of a cell adhesion molecule and an anticoagulant.

2. The modified hydrophobic substrate of claim 1, wherein the polymer comprising a terminal amine is selected from the group consisting of polyethylenimine (PEI), polyethyleneglycol (PEG)-amine, polyalkylene oxide (PAO)-amine, polyallylamine, polyvinylamine, poly(vinylamine-co-vinylformamide), chitosan-amine, and poly(amidoamine).

3. The modified hydrophobic substrate of claim 1, wherein the polymer comprising a terminal amine is covalently bonded to the first layer comprising dopamine.

4. The modified hydrophobic substrate of claim 1, wherein the hydrophobic surface is an oxygen plasma treated surface.

5. The modified hydrophobic substrate of claim 1, wherein the at least one biomolecule is a cell adhesion molecule selected from the group consisting of fibronectin, arginine-glycine-aspartic acid (RGD) peptide, arginine-glycine-aspartic acid-serine (RGDS) peptide (SEQ ID NO:1), leucine-aspartic acid-valine (LDV) peptide, fibronectin CS1 region, laminin, tyrosine-isoleucine-glycine-serine-arginine (YIGSR) peptide (SEQ ID NO:2), proline-aspartic acid-serine-glycine-arginine (PDSGR) peptide (SEQ ID NO:3), lysine-arginine-glutamic acid (LRE) peptide, vitronectin, arginine-glycine-aspartic acid-valine (RGDV) peptide (SEQ ID NO:4), and combinations thereof.

SEQUENCE LISTING

```
Sequence total quantity: 4
SEQ ID NO: 1           moltype = AA  length = 4
FEATURE                Location/Qualifiers
source                 1..4
                       mol_type = protein
                       organism = synthetic construct
SEQUENCE: 1
RGDS                                                                      4

SEQ ID NO: 2           moltype = AA  length = 5
FEATURE                Location/Qualifiers
source                 1..5
                       mol_type = protein
                       organism = synthetic construct
SEQUENCE: 2
YIGSR                                                                     5

SEQ ID NO: 3           moltype = AA  length = 5
FEATURE                Location/Qualifiers
source                 1..5
                       mol_type = protein
                       organism = synthetic construct
SEQUENCE: 3
PDSGR                                                                     5

SEQ ID NO: 4           moltype = AA  length = 4
FEATURE                Location/Qualifiers
source                 1..4
                       mol_type = protein
                       organism = synthetic construct
SEQUENCE: 4
RGDV                                                                      4
```

6. The modified hydrophobic substrate of claim 1, wherein the at least one biomolecule is an anticoagulant selected from the group consisting of heparin, low molecular weight heparin, a coumarin, a directly acting oral anticoagulants, fondaparinux, idraparinux, a factor Xa inhibitor, a thrombin inhibitor, hementin, and combinations thereof.

7. The modified hydrophobic substrate of claim 1, wherein the substrate is selected from the group consisting of glass, metal, wood, cotton, plastic, ceramic, and combinations thereof.

\* \* \* \* \*